United States Patent [19]

Hamprecht

[11] Patent Number: 5,955,615

[45] Date of Patent: Sep. 21, 1999

[54] PYRIDONE-METHIDE AZO DYESTUFFS

[75] Inventor: Rainer Hamprecht, Odenthal, Germany

[73] Assignee: Bayer Aktiengesellschaft, Germany

[21] Appl. No.: 09/080,618

[22] Filed: May 18, 1998

Related U.S. Application Data

[62] Division of application No. 08/715,667, Sep. 18, 1996, Pat. No. 5,808,015.

[30] Foreign Application Priority Data

Sep. 25, 1995 [DE] Germany ............................ 19535501

[51] Int. Cl.$^6$ ..................... C07D 211/78; C07D 211/90; C07D 213/84; C07D 211/72; C07D 211/84; C07D 213/63
[52] U.S. Cl. ......................... 546/286; 546/287; 546/288; 546/290
[58] Field of Search .................. 546/287, 286, 546/288, 290

[56] References Cited

U.S. PATENT DOCUMENTS

| | | | |
|---|---|---|---|
| 2,294,380 | 12/1942 | Braker et al. | 260/156 |
| 2,431,190 | 6/1947 | Morgan et al. | 95/6 |
| 2,888,451 | 5/1959 | Henecka et al. | 260/156 |
| 3,905,951 | 9/1975 | Berrie et al. | 546/288 X |
| 4,061,642 | 12/1977 | Fleckenstein et al. | 546/287 X |
| 4,116,965 | 9/1978 | Desai et al. | 546/287 |
| 4,837,308 | 6/1989 | Gerlach et al. | 534/578 |
| 4,849,522 | 7/1989 | Jones et al. | 546/288 |
| 5,212,314 | 5/1993 | Jones et al. | 546/256 |
| 5,418,245 | 5/1995 | Spada et al. | 514/357 |
| 5,608,041 | 3/1997 | Schefezik et al. | 534/752 |

FOREIGN PATENT DOCUMENTS

| | | |
|---|---|---|
| 491554 | 3/1975 | Australia . |
| 201 892 | 5/1986 | European Pat. Off. . |
| 1 082 598 | 6/1960 | Germany . |
| 2 015 172 | 3/1970 | Germany . |
| 40 20 768 | 1/1992 | Germany . |
| 43 26 758 | 2/1995 | Germany . |
| 43 29 296 | 3/1995 | Germany . |
| 1326 124 | 3/1970 | United Kingdom . |
| 2 036 775 | 7/1990 | United Kingdom . |

OTHER PUBLICATIONS

Junek, et al., International Journal of Methods in Synthetic Organic Chemistry, Synthesis (1977), p. 560.

Taylor, et al. "The Reaction of Malononitrile with Hydrazine", The Journal of the American Chemical Society, (1959) vol. LXXXI, Apr.–Jun., pp. 2452–2455.

Cossey et al., "Pyridines and Pyridinium Salts from Cyanoacetamides", Aust. J. Chem. ., (1976) 29, pp. 1039–1050.

Sadek et al., "Activated Nitriles in Heterocyclic Synthesis. Synthesis of Several New Pyrimidine and Pyridazine Derivatives", Journal of Chemical and Engineering Data, (1984), vol. 29, pp. 101–103.

Ivanov et al., "Selbstkondensation des 3–Amino–3–ethoxypropensäure–ethyl–esters und verwandte Reaktionen", Liebigs Annalen Der Chemie, (1983), pp. 753–760.

Mittelbach et al., "3–Amino–4,4–dicyan–3–butensäureester, ein Synthesebaustein aus der Reihe der Dimeren von Malononitril und Cyanessigester", Liebigs Ann. Chem. (1986), pp. 533–544.

Mittelbach, et al., "Untersuchungen zur Struktur der Dimeren des Malononitrils, Cyanessigesters und Cyanacetamids", Synthesen mit Nitrilen, LXXVIII (1987), pp. 1131–1132.

Inoue, et al., "Syntheses of 4–Hydroxy–2–Phenylazo–1,3, 5–Triazines by Oxidating Coupling of 2–Hydrazino–4–Hydroxy–1,3,5–Triazines With N,N–Di––Alkylanilines", Chemistry Express, vol. 3, No. 7, (1988) pp. 423–426

Müller et al., "V. Herstellung von Diarylazoverbindungen durch die oxydative Kupplung", Methoden Der Organischen Chemie (1965) pp. 360–371.

Sykes., Reaktionsmechanismen der Organischen Chemie, (1988), 9$^{th}$ Edition, pp. 426–429.

Junek et al., "Die Enamin–Lacton–Umlagerung von Benzopyron–amino–acrylsäureestern", Montashefte für Chemie 101, (1970) pp. 1208–1214.

Junek et al., "Zur Synthese von Dihydropyridinen aus Enaminoketonen mit Malonitril", Montashefte für Chemie, (1964) 95, 1201 pp. 1473–1478.

Junek et al., "Ringschlüsse zu 1, 2–Dihydropyridinen", R. Hull J. Chem. Soc. (1951) 1136, pp. 1202–1206.

Textiles Paper: Cellulose, J5–F, Week 8343, p. 9 (1983).

*Primary Examiner*—Floyd D. Higel
*Attorney, Agent, or Firm*—Connolly & Hutz

[57] ABSTRACT

Dyestuffs of the formula (I)

$$D-N=N-\underset{\underset{A^5}{|}}{\underset{H-X}{\overset{A^1}{\diagdown}}}\text{pyridine ring with } A^2, A^3, A^4 \text{ substituents} \left[ \begin{array}{l} (SO_3H)_m, \\ (Z)_n \\ K_1^{\oplus} B_1^{\ominus} \end{array} \right.$$

wherein

D is the radical of a carbo- or heterocyclic diazo component,

X represents O, NH, NT, NCOT, NCCH$_2$T or NSO$_2$T, and the other substituents have the meaning given in the description, are preferably suitable, if m=n=l=o, for dyeing and printing hydrophobic synthetic fiber materials and mixtures thereof with naturally occurring fiber materials.

9 Claims, No Drawings

PYRIDONE-METHIDE AZO DYESTUFFS

This is a division of Ser. No. 08/715,667 filed Sep. 18, 1996, now U.S. Pat. No. 5,808,015.

The invention relates to pyridone-methide azo dyestuffs, processes for their preparation, their use and coupling components containing pyridone-methide.

Azo dyestuffs which contain a coupling component based on methylene-triazolo-pyridines are already known from DE-A 4 020 768 and DE-A 4 329 296. However, these azo dyestuffs still have some disadvantages in their use. Thus, for example, their build-up capacity and their stability in the dyebath when used for dyeing polyester is not satisfactory.

Pyridone-methide azo dyestuffs have now been found, which, in the form of the free acid, correspond to the formula (I) or its tautomeric forms

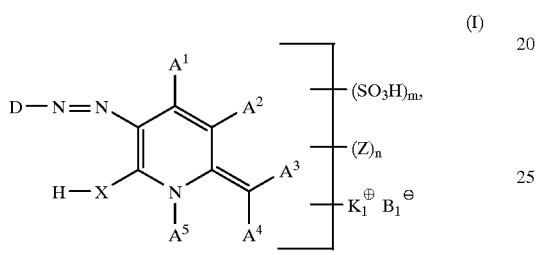

(I)

wherein
D is the radical of a carbo- or heterocyclic diazo component, $A^1$ and $A^2$ independently of one another denote H or a substituent typical for pyridones, $A^3$ and $A^4$ independently of one another denote an electron-withdrawing radical, or, together with the common C atom, form a cyclic methylene-active compound, $A^5$ represents H or a radical of the formula T, $-OT^1$, $-NH_2$, -NHT, $-NT_2$, -NHCOH, -NHCOT, $-N=CH-T$, $-N=CT_2$ or $NHSO_2T$, wherein
$T^1$=alkyl, cycloalkyl or aralkyl, and T represents $T^1$ or can assume the meaning of $T^2$ to $T^5$, where $T^2$=alkenyl,
$T^3$=alkinyl,
$T^4$=aryl,
$T^5$=hetaryl or
$A^1$ and $A^1$ and/or
$A^2$ and $A^3$ and/or
$A^4$ and $A^5$, together with the particular atoms in between, form an unsaturated, optionally substituted 5- or 6-membered carbo- or heterocyclic radical, with the proviso that if a ring is formed with participation of one of the two radicals $A^3$ and $A^4$, the radical which does not participate denotes an electron-withdrawing radical,
X represents O, NH, NT, NCOT, $NCO_2T$ or $NSO_2T$,
$K^\oplus$ is $-NH_3^\oplus$, $-NHT_2^\oplus$, $-NH_2T^\oplus$, $-NT_3^\oplus$ or a cycloimmonium ion,
$B^\ominus$ is an anion,
Z is a fibre-reactive radical,
l represents 0 to 2,
m represents 0 to 8 and
n represents 0 to 6.

Preferred pyridone-methide azo dyestuffs are those which correspond to the formula (I) or its tautomeric form wherein $A^1$ and $A^2$ independently of one another denote H or a radical of the formula T, -COH, -CO-T, $-CO_2T$, -CN, $-CONH_2$, -CONHT, $-CONT_2$, $CF_3$, $-NH_2$, -NHT, $-NT_2$, -NH-COT, -NT-COT, $-NHSO_2T$, $-NTSO_2T$, $-NO_2$, -NO, $-SO_2T$, -OH, -OT, -OCOT, $-OCO_2T$, $-OSO_2T$, Cl, Br or I wherein
T can assume the meaning of $T^1$, $T^2$, $T^3$, $T^4$ or $T^5$.

The dyestuffs of the formula (I) according to the invention can exist in various tautomeric forms. One form corresponds, for example, to the formula (I), another corresponds, for example, to the following formula

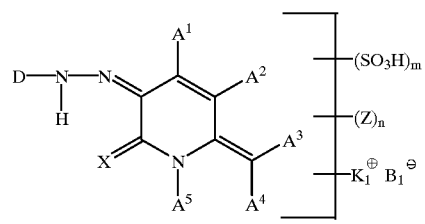

An electron-withdrawing radical is preferably understood as meaning a radical of which the Hammett substituent constant σ (para) is >0, one of the two substituents $A^3$ or $A^4$ preferably having a σ (para) value >0.300. An appropriate list of Hammett substituent constants is to be found, for example, in Sykes, Reaktionsmechanismen der organischen Chemie [Reaction mechanisms of organic chemistry], 9th Edition, Weinheim, VCH Verlagsgesellschaft, 1988, or can be determined by known methods.

$T^1$ preferably represents $C_1$-$C_{20}$-alkyl, $C_4$-$C_8$-cycloalkyl or $C_6$-$C_{10}$-aryl-$C_1$-$C_8$-alkyl, each of which is unsubstituted or substituted by one or more substituents from the group consisting of OH, $C_1$-$C_{10}$-alkoxy,

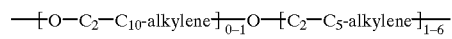

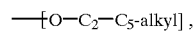,

-OCOH, COH, -OCOT, $-OSO_2T$, $-O(CH_2CH_2O)_{1-6}COT$, $-OCO_2T$, COT, $-SO_2T$, $-CO_2T$, -CN, $-CONH_2$, -CONHT, $-CONT_2$, $-CO_2H$, $-SO_2NH_2$, $-SO_2NHT$, $-SO_2NT_2$, $-CF_3$, $-NO_2$ and halogen.

$T^2$ and $T^3$ independently of one another preferably represent $C_2$-$C_{20}$-alkenyl or $C_2$-$C_{20}$-alkinyl, each of which is unsubstituted or substituted by one or more substituents from the group of substituents already mentioned under $T^1$.

$T^4$ preferably represents $C_6$-$C_{16}$-aryl, which is unsubstituted or substituted by one or more substituents from the group of substituents already mentioned under $T^1$, further possible substituents being $-NH_2$, -NHT, $-NT_2$, -NHCOH, -NHCOT, $NHSO_2T$, $C_2$-$C_{10}$-alkenyl, $C_2$-$C_{10}$-alkinyl, $C_1$-$C_{10}$-alkyl, $C_4$-$C_8$-cycloalkyl and $C_6$-$C_{10}$-aryl-$C_1$-$C_6$-alkyl.

$T^5$ preferably represents a 5- or 6-membered aromatic heterocyclic radical which contains 1 to 3 identical or different hetero atoms from the group consisting of N, O, S, NH, SO and $SO_2$ and is unsubstituted or substituted by one or more substituents from the group of substituents already mentioned under $T^1$ and is optionally fused with one or two aryl or hetaryl rings.

Preferred dyestuffs of the formula (I) are those wherein l=1 or 2 and n=0, and m is less than 1, and is preferably 0, which are called "cationic dyestuffs" of the formula (I) below.

Dyestuffs which are likewise preferred are those of the formula (I) wherein l=m=n=0, which are called "disperse dyestuffs of the formula (I)" below.

Dyestuffs which are furthermore preferred are those of the formula (I) wherein l=0 and m and/or n are not equal to 0. These dyestuffs according to the invention are called "acid dyestuffs of the formula (I)" below, if n is 0, and "reactive dyestuffs of the formula (I)" below, if n is not equal to 0.

Acid dyestuffs of the formula I are also understood as meaning those which carry COOH groups and wherein m is 0.

Disperse dyestuffs

Preferred disperse dyestuffs of the formula (I) are those in which $A^3$ and $A^4$ independently of one another represent -CN, $-CO_2T$, $-CONH_2$, -CONHT, $-CONT_2$, $CF_3$, -CHO, -COT, $-SO_2T$, $-SO_3T^4$, $-SO_3T^5$, $SO_2NH_2$, $SO_2NHT$, $SO_2NT_2$, -SOT, -CH=NH, -CH=NT, -CT=NH, -CT=NT,

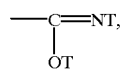

$-CO-CO_2T$, $-NO_2$, NO, $T^4$ or $T^5$, wherein $A^3$ and $A^4$ preferably do not simultaneously represent $T^4$ and/or $T^5$, or $A^3$ and $A^4$, together with the C atom to which they are bonded, represent a cyclic methylene-active compound of the formula (IIa) to (IIv), where these radicals are shown in the form of

(II)

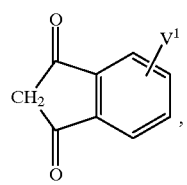
(IIa)

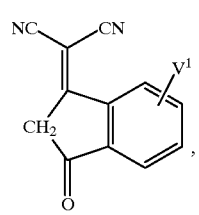
(IIb)

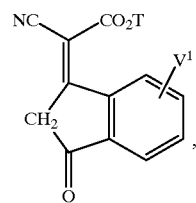
(IIc)

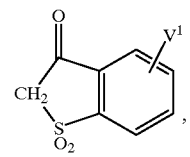
(IId)

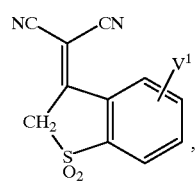
(IIe)

(IIf)

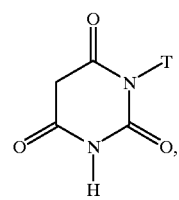
(IIg)

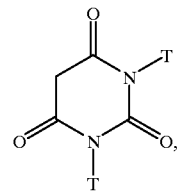
(IIh)

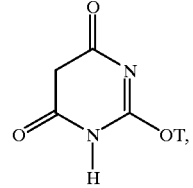
(IIi)

-continued (IIj) 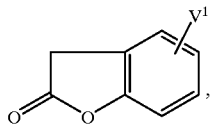

(IIk) 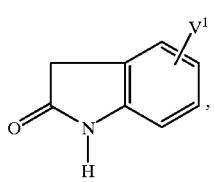

(IIl) 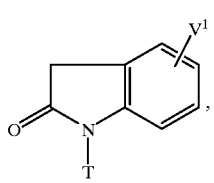

(IIm) 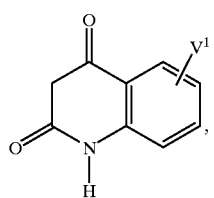

(IIn) 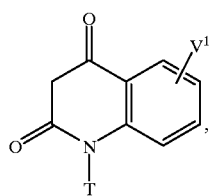

(IIo) 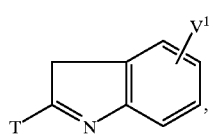

(IIp) 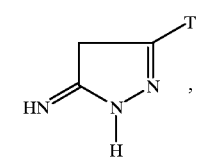

(IIq) 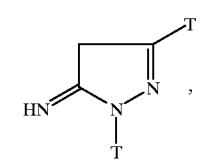

-continued (IIr) 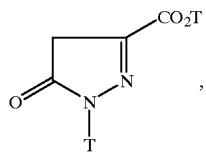

(IIs) 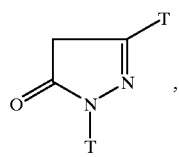

(IIt) 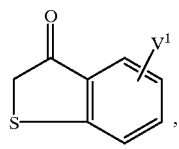

(IIu) 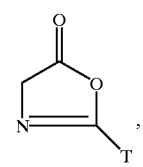

(IIv) 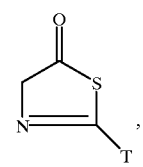

wherein $V^1$ represents H or a substituent, in particular Cl, Br, $CH_3$, $-CO_2T^1$, -CN, $-NO_2$, $-CF_3$ or $-SO_2T^1$, and wherein $A^1$, $A^2$, $A^5$, D and X have the abovementioned meanings.

Preferred disperse dyestuffs of the formula (I) are those wherein $A^1$ represents H, T, -COH, -COT, $-CO_2T$, -CN, $-CONH_2$, $-CONH_2$, -CONHT, $-CONT_2$, $CF_3$, OH or halogen, in particular Cl, Br and I, $A^2$ represents H, T, -COH, -COT, -CN, $-CO_2T$, $-CONH_2$, -CONHT, $-CONT_2$, $-CF_3$, $-NO_2$, -NO, Cl, Br or I, $A^3$ and $A^4$ independently of one another represent -CN, $-CO_2T$, $-CONH_2$, -CONHT, $-CONT_2$, $CF_3$, -CHO, -COT, $-SO_2T$, $-SO_3T^4$, $-SO_3T^5$, $SO_2NH_2$, $SO_2NHT$, $SO_2NT_2$, -SOT, -CH=NH, -CH=NT, -CT=NH, -CT=NT, $-CO-CO_2T$, $-NO_2$, -NO, $T^4$ or $T^5$, wherein $A^3$ and $A^4$ preferably do not simultaneously represent $T^4$ and/or $T^5$, or $A^2$ and $A^3$, together with the C atoms in between them, form the radical of a fused indene ring which is optionally substituted by $R^1$, or $A^3$ and $A^4$, together with the C atom to which they are bonded, form a carbocyclic or heterocyclic radical of the formula (IIa) to (IIv), $A^5$ denotes H, $T^1$, $T^2$, $T^3$, $T^4$, $-NH_2$, -NHT, $NT_2$, -NHCOT, -NHCOH, $-NHSO_2T$ or $-N=CT_2$ or $A^4$ and $A^5$, together with the atoms of the pyridone ring in between, form a fused ring of the formula

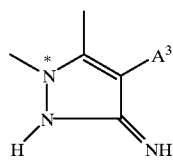

wherein the N atom labelled with corresponds to the pyridone nitrogen, $T^1$ denotes $C_1$-$C_{10}$-alkyl, $C_5$-$C_7$-cycloalkyl or $C_6$-$C_{10}$-aryl-$C_1$-$C_6$-alkyl, which are optionally substituted by one or more substituents from the group consisting of -OH, -$C_1$-$C_{10}$-alkoxy, -O[(CH$_2$)$_{2-10}$-O]$_{1-6}$-alkyl, in particular -$C_1$-$C_{10}$-alkoxy-$C_2$-$C_5$-alkoxy, -$C_1$-$C_5$-alkoxy-$C_2$-$C_5$-alkoxy-$C_2$-$C_5$-alkoxy or -O-(CH$_2$-CH$_2$O)$_{1-6}$-alkyl, -OCOT, -OSO$_2$T, -O-(CH$_2$-CH$_2$O)$_{1-6}$-COT, -COT, -SO$_2$T, -CO$_2$T, -CN, -CO$_2$H, -CONT$_2$, -CF$_3$, Cl, Br and I, $T^2$ and $T^3$ independently of one another denote $C_2$-$C_{10}$-alkenyl or alkinyl, which are optionally substituted by one or more substituents from the group consisting of OH, -$C_1$-$C_6$-alkoxy, -OCOT, -OCOH, -CO$_2$T, -CO$_2$H, -CN, Cl, Br and I, $T^4$ denotes phenyl, which is optionally substituted by one or more substituents such as -$C_1$-$C_{10}$-alkoxy, -(O-$C_2$-$C_{10}$-alkylene)$_{0-1}$-O-($C_2$-$C_5$-alkylene)$_{1-6}$-O-($C_2$-$C_5$-alkyl) in particular $C_1$-$C_{10}$-alkoxy-$C_2$-$C_5$-alkoxy, $C_1$-$C_5$-alkoxy-C2-$C_5$-alkoxy-$C_2$-$C_5$-alkoxy, -OCOH, -OCOT, -OSO$_2$T, -COH, -COT, -SO$_2$T, -CO$_2$T, -CN, -CF$_3$, -CCl$_3$, -NO$_2$, -NO, -CO$_2$H, -CONH$_2$, -CONHT, -CONT$_2$, -SO$_2$NT$^2$, -$C_1$-$C_{10}$-alkyl, optionally substituted by -OH, -CN, -CO$_2$-$C_1$-$C_6$-alkyl, Cl, Br or I, -$C_2$-$C_{10}$-alkenyl, optionally substituted by -OH, -CN, -CO$_2$-$C_1$-$C_6$-alkyl, Cl, Br or I, and -$C_2$-$C_{10}$-alkinyl, optionally substituted by $C_1$-$C_{10}$-alkoxy, -OH, -OCOH, -OCOT, Cl, Br or I, $T^5$ denotes thiophene, furan, pyrrole, 1,2-isothiazole, 1,3-thiazole, pyrrazole, oxazole, isooxazole, imidazole, triazole, pyridine, pyridazine, pyrimidine, pyrazine, triazine, oxazine, benzothiazole, benzimidazole, benzoxazole, quinoline, isoquinoline, indole, coumarone, thionaphthene or tetrazole, optionally substituted by 1 to 3 substituents such as are already described as substituents for phenyl, X denotes O, -NCOT, -NCO$_2$T or -NSO$_2$T, D denotes a radical of the formula (IIIa) to (IIIu)

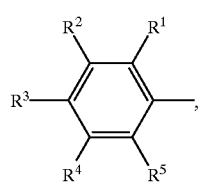
(IIIa)

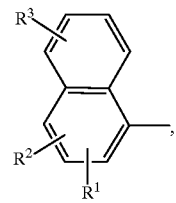
(IIIb)

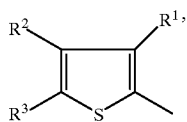
(IIIc)

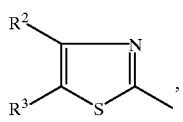
(IIId)

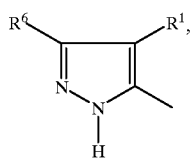
(IIIe)

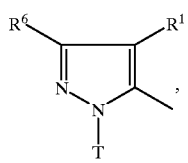
(IIIf)

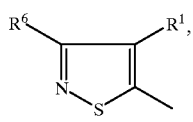
(IIIg)

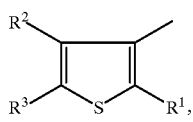
(IIIh)

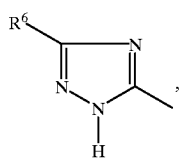
(IIIi)

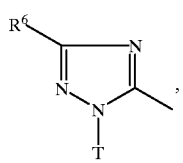
(IIIj)

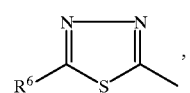 (IIIk)

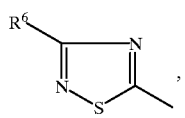 (IIIl)

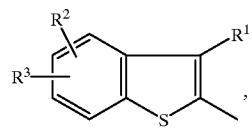 (IIIm)

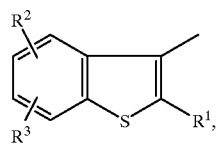 (IIIn)

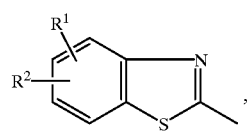 (IIIo)

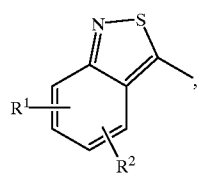 (IIIp)

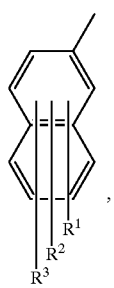 (IIIq)

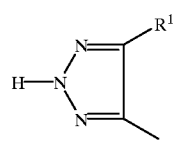 (IIIr)

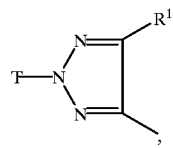 (IIIs)

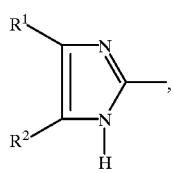 (IIIt)

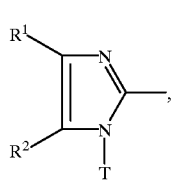 (IIIu)

$R^1$, $R^2$, $R^3$, $R^4$, $R^5$ and $R^6$ independently of one another and denotes H, T, F, Cl, Br, I, -CN, -NO$_2$, -CH=O, -COT, -CO$_2$T$^1$, -CONH$_2$, -CONHT, CONT$_2$, -CF$_3$, -SO$_2$NH$_2$, -SO$_2$NHT, -SO$_2$NT$_2$, -SOT, -SO$_2$T, -SO$_3$T, -OT, -OH, -OCOT, -OCO$_2$T, -OSO$_2$T, -NH$_2$, -NHT, -NT$_2$,

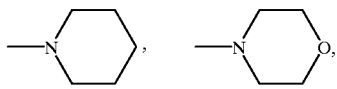

-NHCOH, -NHCOT, -NHSO$_2$T or -COCO$_2$T, wherein
$R^3$ can additionally denote -N=N-T$^4$ or -N=N-T$^5$ and
$R^6$ can additionally denote ST.

Particularly preferred disperse dyestuffs of the formula (I) are those wherein $A^1$ denotes H, T$^1$, T$^4$ or -CF$_3$, $A^2$ denotes H, -CN, -CO$_2$T$^1$, -CONHT$^1$ or -CF$_3$, $A^3$ and $A^4$ independently of one another denote -CN-, -CO$_2$T$^1$, -CONHT$^1$, -CF$_3$, -CHO, -COT, -SO$_2$T, -NO$_2$, -T$^4$ or -T$^5$, wherein $A^3$ and $A^4$ do not simultaneously represent T$^4$ or T$^5$, $A^3$ and $A^4$, together with the C atom to which they are bonded, form a cyclic methylene-active compound of the formula (IIa), (IId) or (IIh), where the radicals of the cyclic methylene-active compound are shown in the form of

 (II)

$A^5$ is H, T$^1$, T$^2$ or T$^4$, or $A^4$ and $A^5$, together with the atoms in between, form a fused ring of the formula

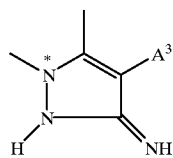

in which the N atom marked with * corresponds to the pyridone nitrogen,

D denotes a radical of the formula

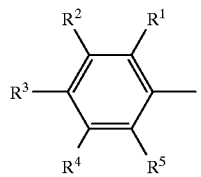

wherein $R^1$ and $R^5$ independently of one another represent H, $CF_3$, Cl, Br, -CN, $-NO_2$, $-CO_2T^1$, $T^1$, $T^5$,$-SO_2T^1$, $-SO_2T^4$, $-OT^1$, $-OT^2$, $-OT^4$, $-OCOT^1$, $-OCOT^4$, $-OSO_2T^1$ or $-OSO_2T^4$, $R^2$ and $R^4$ independently of one another denote H, Cl, Br, $-NO_2$, $-CF_3$, $T^1$, $-OT^1$, $-OT^2$, $-OT^4$, $-OCOT^1$, $-OCOT^4$, $OSO_2T^1$ or $-OSO_2T^4$, $R^3$ represents H, Cl, Br, -CN, $-NO_2$, $-CF_3$, $-CO_2T^1$, $T^1$, $T^5$, $-OT^1$, $-OT^2$, $-OT^4$, $-OCOT^1$, $-OCOT^4$, $-SO_3T^1$ or $-SO_2T^4$, $T^1$ represents $C_1$-$C_8$-alkyl, which is optionally substituted by $-C_1$-$C_8$-alkoxy, $-C_1$-$C_8$-alkoxy-$C_2$-$C_5$-alkoxy, $-OCOT^1$, $-CO_2T^1$, Cl, Br, -CN or $T^4$, $T^2$ represents $C_2$-$C_8$-alkenyl, which is optionally substituted by $-C_1$-$C_8$-alkoxy, $-C_1$-$C_8$-alkoxy-$C_2$-$C_5$-alkoxy, -CN, $-CO_2T^1$, Cl or Br, $T^4$ represents phenyl, which is optionally substituted by Cl, Br, $T^1$, $OT^1$, $-CF_3$, $-NO_2$, -CN or $-CO_2T^1$, $T^5$ denotes oxazole, phenyloxazole, benzoxazole, thiazole, benzothiazole, thiadiazole or thiophene, which is optionally substituted by Cl, Br, $T^1$, $-NO_2$ and/or $-CO_2T^1$ and X denotes O.

Especially preferred disperse dyestuffs of the formula (I) are those wherein $A^1$ represents H, $T^1$ or $-CF_3$, $A^2$ denotes H, -CN or $-CO_2T^1$, $A^3$ represents -CN or $-CO_2T^1$, $A^4$ denotes $A^3$, or $A^3$ and $A^4$, together with the C atom to which they are bonded, form a cyclic methylene-active compound of the formula (IIa) or (IId), where the radicals of the cyclic methylene-active compound are shown in the form of

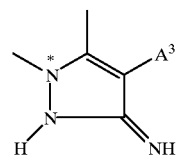

$A^5$ represents H, $T^1$ or $T^2$,

D represents a radical of the formula

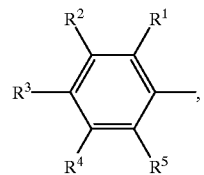

wherein $R^1$ and $R^5$ independently of one another denote H, Cl, Br, -CN, $-NO_2$, $-CO_2T^1$, $T^1$, $-OT^1$ or $-OT^4$, $R^2$ and $R^4$ independently of one another denote H, Cl, Br, $-NO_2$, $T^1$ or $-OT^1$, $R^3$ represents H, Cl, Br, -CN, $-NO_2$, $T^1$, $-CO_2T^1$ or $-OT^1$, $T^1$ represents $C_1$-$C_6$-alkyl or $C_1$-$C_4$-$T^4$, optionally substituted by $C_1$-$C_6$-alkoxy, $-C_1$-$C_4$-alkoxy-$C_2$-$C_5$-alkoxy or $-CO_2T^1$, $T^2$ denotes $C_2$-$C_6$-alkenyl which is optionally substituted by Cl and/or Br, $T^4$ represents phenyl, which is optionally substituted by Cl, Br, $-NO_2$ and/or $-CO_2T^1$ and X denotes 0.

The disperse dyestuffs of the formula I according to the invention have a good fastness to light, high tinctorial strength and high affinity on polyester, and dye polyester in brilliant shades.

Cationic dyestuffs

Preferred cationic dyestuffs of the formula (I) are those wherein $A^1$ to $A^5$ and X have the meanings given for the disperse dyestuffs of the formula (I) and D represents a radical of the formula (IIIa) to (IIIu), preferably (IIIa), wherein $K^\oplus$ is bonded to one or more positions, as desired, of the radicals D and/or $A^1$ to $A^5$, $B^\ominus$ denotes an anion, l represents 1 or 2 and m is preferably 0.

Preferred anions $B^\ominus$ are colourless, organic and inorganic anions, for example fluoride, chloride, bromide, iodide, perchlorate, tetrafluoroborate, hydroxide, hydrogen sulphate, sulphate, dihydrogen phosphate, hydrogen phosphate, phosphate, bicarbonate, carbonate, methyl-sulphate, ethyl-sulphate, cyanate, thiocyanate, tri- and tetrachlorozincate, tetrachloroferrate, hexafluorosilicate and anions of saturated or unsaturated aliphatic, cycloaliphatic, aromatic or heterocyclic carboxylic and sulphonic acids, such as formate, acetate, hydroxyacetate, cyanoacetate, propionate, hydroxypropionate, oxalate, citrate, lactate, tartrate, the anion of cyclohexanecarboxylic acid, phenylacetate, benzoate, the anion of nicotinic acid, methanesulphonate, ethanesulphonate, benzenesulphonate, chlorobenzenesulphonate and toluenesulphonate. If the anions are polyvalent, for example sulphate or oxalate, $B^\ominus$ in formula (I) represents one equivalent of such a polyvalent anion.

Preferred cationic diazo components D are radicals $D^1$ of the formula

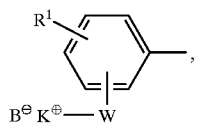

wherein $R^1$, $K^\oplus$ and $B^\ominus$ have the abovementioned meaning and

W denotes a direct bond or a bridge member.

Possible bridge members W are, for example, the following radicals:

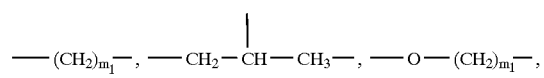
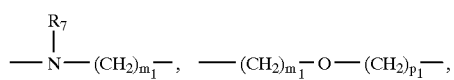
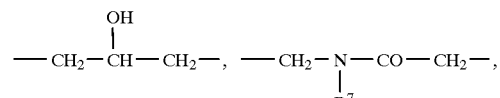
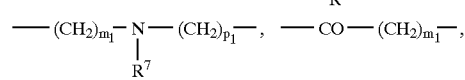
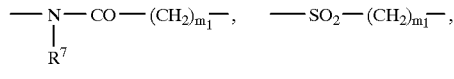
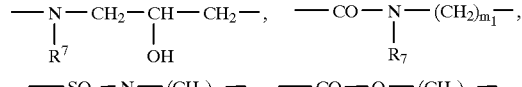
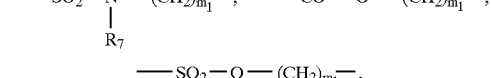
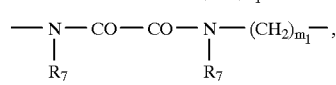
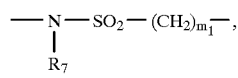
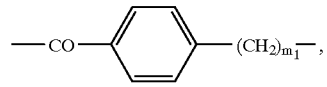
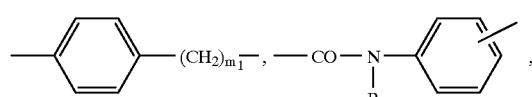
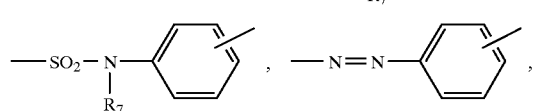
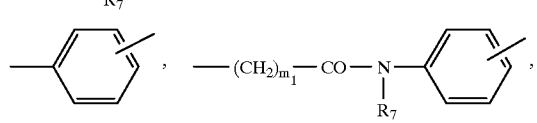

wherein $R_7$ denotes hydrogen, methyl or ethyl and $m_1$ and $p_1$ independently of one another represent any number from 1 to 4.

Suitable radicals $K^\oplus$ are, for example:

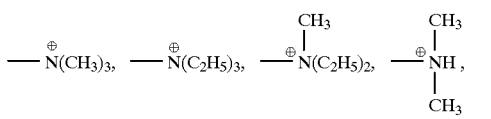
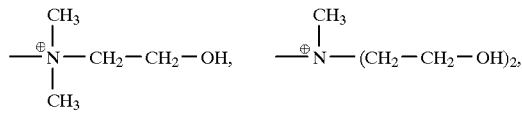
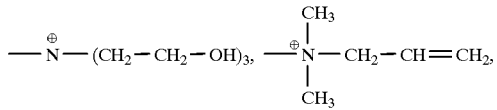
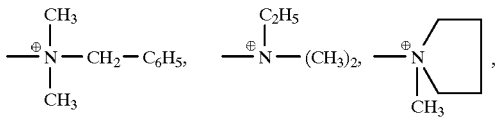
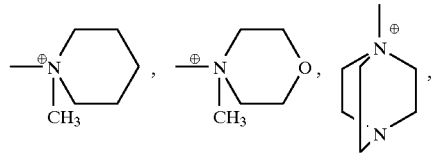
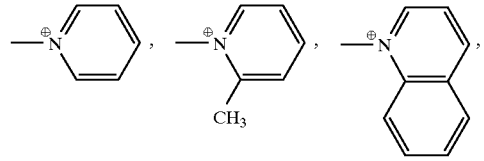
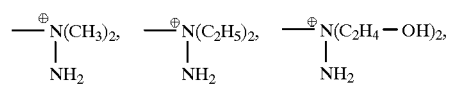
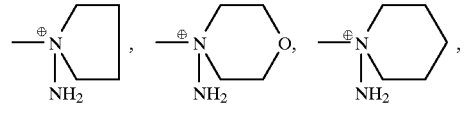
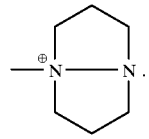

Acid dyestuffs

Preferred acid dyestuffs of the formula (I) are those wherein D, $A^1$ to $A^5$ and X have the meanings given for the disperse dyestuffs of the formula (I), at least one $SO_3H$ group and/or one COOH group being bonded to at least one of these radicals. Particularly preferred acid dyestuffs of the formula (I) are those wherein m denotes 1 to 4.

Radicals D containing sulphonic acid groups are, for example, radicals $D^2$, wherein $D^2$ is a phenyl, phenylazophenyl or naphthyl radical which carries 1 or 2 $SO_3H$, $OSO_3H$ or phenyl-$SO_2$-NH-$SO_2$ groups and is optionally substituted one to four times by $C_1$-$C_4$-alkyl, $C_1$-$C_4$-alkoxy, trifluoromethyl, $C_1$-$C_4$-alkylcarbonylamino, benzoylamino, $C_1$-$C_4$-alkylsulphonylamino, benzenesulphonylamino, cyano, halogen, nitro, $C_1$-$C_4$-alkylsulphonyl, phenylsulphonyl, tolylsulphonyl, chlorophenylsulphonyl, carboxyl, $C_1$-$C_4$-alkoxycarbonyl, aminocarbonyl, aminosulphonyl, N-mono- or di-$C_1$-$C_4$-alkyl-substituted aminocarbonyl or -sulphonyl, or by one benzothiazolyl.

Suitable radicals $D^2$ correspond, in the form of their diazo components, for example, to the following:

1-Aminobenzene-2-, -3- or -4-sulphonic acid, 1-aminobenzene-2,4- or -2,5-disulphonic acid, 1-amino-2-methylbenzene-4-sulphonic acid, 1-amino-3-methylbenzene-4-sulphonic acid, 1-amino-4-methylbenzene-2- or -3-sulphonic acid, 2-nitroaniline-4-sulphonic acid, 4-nitroaniline-2-sulphonic acid, 2-chloroaniline-4- or -5-sulphonic acid, 3-chloroaniline-6-sulphonic acid, 4-chloroaniline-2-sulphonic acid, 1-amino-3,4-dichlorobenzene-6-sulphonic acid, 1-amino-2,5-dichlorobenzene-4-sulphonic acid, 1-amino-4-methyl-5-chlorobenzene-2-sulphonic acid, 1-amino-3-methyl-4-chlorobenzene-6-sulphonic acid, 2-amino-4-sulphobenzoic acid, 1-amino-4-acetaminobenzene-2-sulphonic acid, 1-amino-5-acetaminobenzene-2-sulphonic acid, 1-amino-2-methoxy-4-nitrobenzene-5-sulphonic acid, 1-aminonaphthalene-2- or 4-sulphonic acid, 2-aminonaphthalene-1-sulphonic acid and the diazo components of the formulae

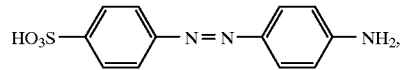

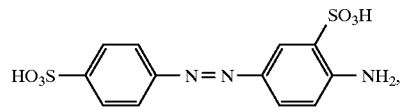

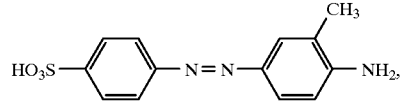

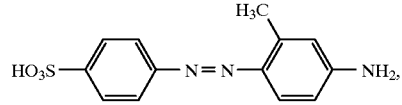

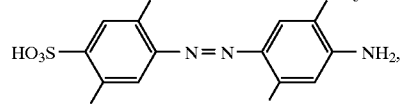

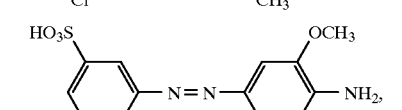

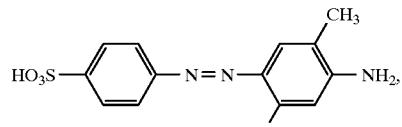

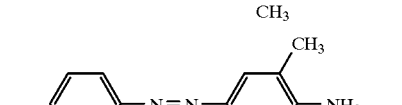

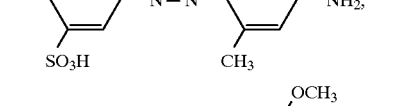

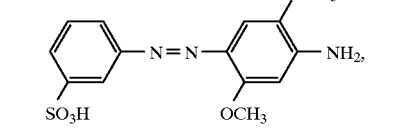

-continued

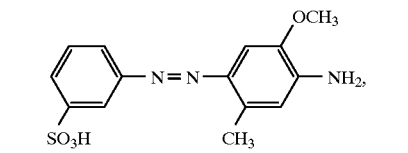

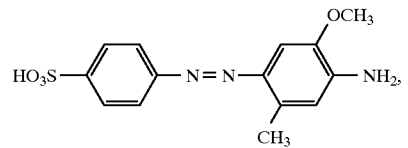

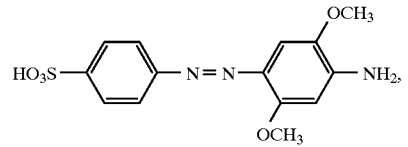

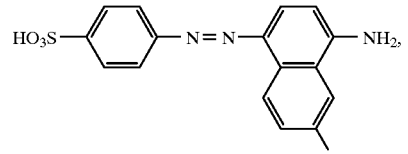

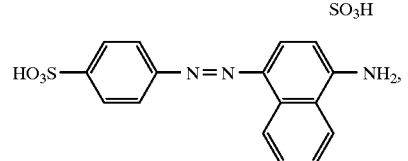

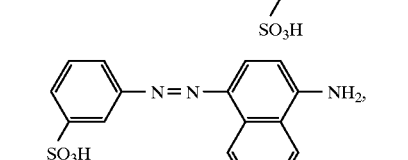

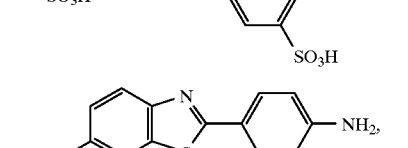

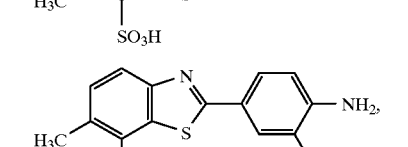

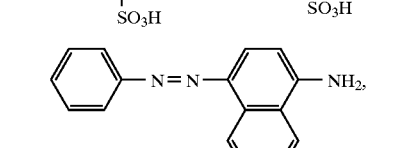

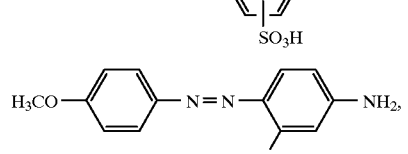

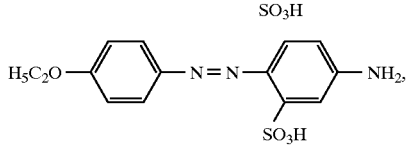

-continued
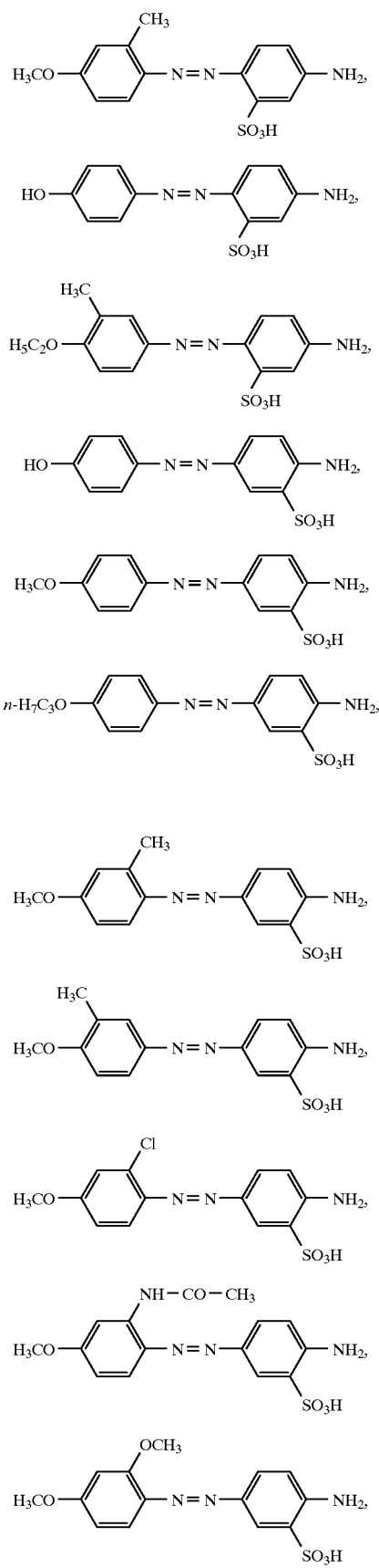
-continued
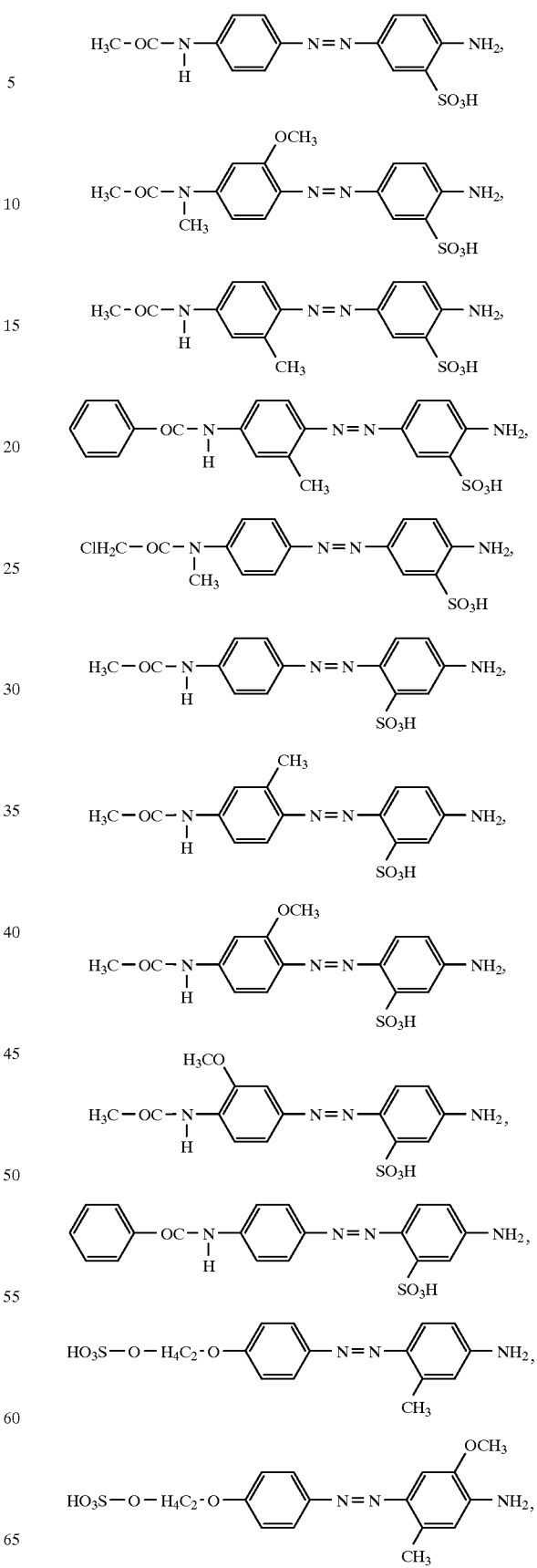

-continued

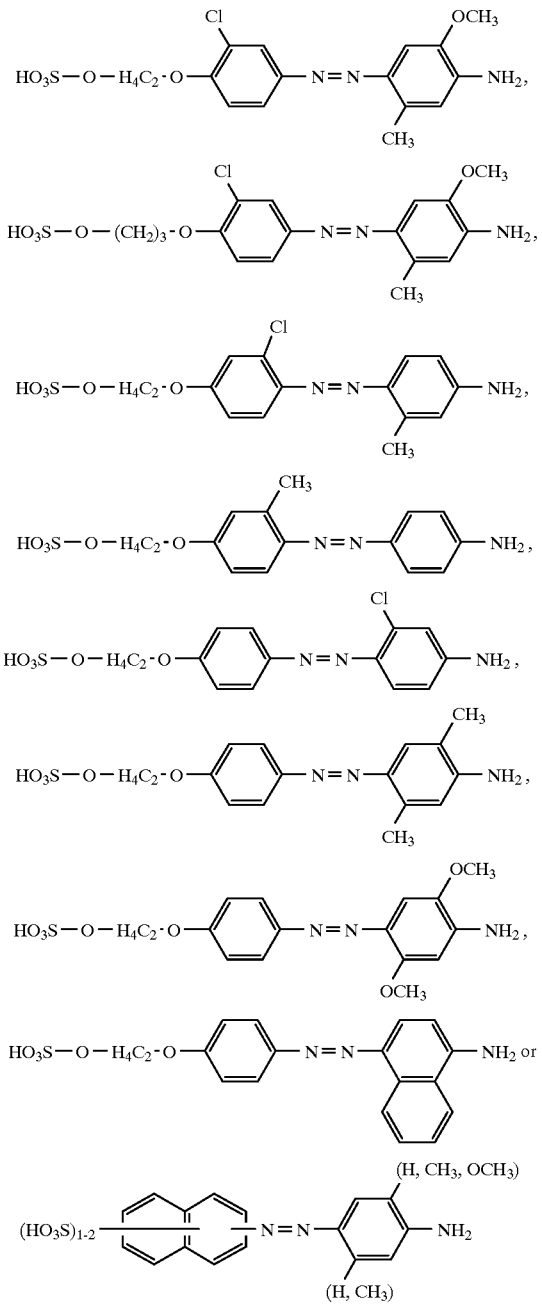

Reactive dyestuffs

Preferred reactive dyestuffs of the formula (I) are those wherein D, $A^1$ to $A^5$ and X have the meanings given for the disperse dyestuffs of the formula (I), an $SO_3H$ group and/or a COOH group preferably being bonded to at least one of these radicals, and wherein one or more identical or different fibre-reactive radicals Z are bonded to at least one of the radicals mentioned.

Reactive dyestuffs of the formula (I) where n=1 to 3 are preferred.

Preferred fibre-reactive radicals are, for example, those of the formula $-CH=CH_2$ or $-CH_2CH_2-V$, wherein V=OH $OSO_3H$, $SSO_3H$, $OCOCH_3$, $OPO_3H_2$, $OSO_2CH_3$, SCN, $NHSO_2CH_3$, Cl, Br, F, $OCOC_6H_5$, $OSO_2-C_6H_4$, $[N(CH_3)_3]^\oplus$ anion$^\ominus$ or an optionally substituted pyridinium radical (substituents on the pyridinium $C_1$-$C_4$-alkyl, COOH, $SO_3H$, CN or carboxamide) (anion=for example, Cl, $HSO_4^\ominus$, $HCO_3^\ominus$ and the like), or heterocyclic fibre-reactive radicals.

Suitable fibre-reactive radicals Z, i.e. those which react with the OH or NH groups of the fibre under dyeing conditions to form covalent bonds, are preferably those which contain at least one reactive substituent bonded to a 5- or 6-membered aromatic-heterocyclic ring, for example to a monoazine, diazine or triazine ring, in particular a pyridine, pyrimidine, pyridazine, pyrazine, thiazine, oxazine or asymmetric or symmetric triazine ring, or to such a ring system which contains one or more fused-on aromatic-carboxylic rings, for example a quinoline, phthalazine, cinnoline, quinazoline, quinoxaline, acridine, phenazine or phenanthridine ring system, and which are not bonded to a further chromophore.

Examples which may be mentioned of the reactive substituents on the heterocyclic radicals are halogen (Cl, Br or F), ammonium, including hydrazinium, pyridinium, picolinium, carboxypyridinium, sulphonium, sulphonyl, azido ($N_3$), thiocyanato, thiolether, oxy-ether, sulphinic acid and sulphonic acid.

The following radicals may be mentioned specifically as examples of Z: 2,4-Difluorotriazin-6-yl, 2,4-dichlorotriazin-6-yl and monohalogeno-sym.-triazinyl radicals, which are substituted by alkyl, aryl, amino, monoalkylamino, dialkylamino, aralkylamino, arylamino, morpholino, piperidino, pyrrolidino, piperazino, alkoxy, aryloxy, alkylthio or arylthio, where alkyl denotes optionally substituted $C_1$-$C_4$-alkyl, aralkyl denotes optionally substituted phenyl-$C_1$-$C_4$-alkyl and aryl denotes optionally substituted phenyl or naphthyl, and the substituents for alkyl are halogen, hydroxyl, cyano, dialkylamino, morpholino, $C_1$-$C_4$-alkoxy, carboxyl, sulpho or sulphato, and the substituents for phenyl and naphthyl are sulpho, $C_1$-$C_4$-alkyl, $C_1$-$C_4$-alkoxy, carboxyl, halogen, acylamino, hydroxyl and amino. Further radicals to be mentioned are 2-amino-4-fluorotriazin-6-yl, 2-methylamino-4-fluorotriazin-6-yl, 2-ethylamino-4-fluorotriazin-6-yl, 2-isopropylamino-4-fluoro-triazin-6-yl, 2-dimethylamino-4-fluorotriazin-6-yl, 2-diethylamino-4-fluorotriazin-6-yl, 2-β-methoxy-ethylamino-4-fluoro-triazin-6-yl, 2-β-hydroxyethylamino-4-fluoro-triazin-6-yl, 2-di-(β-hydroxyethylamino)-4-fluorotriazin-6-yl, 2-carboxymethylamino-4-fluoro-triazin-6-yl, 2-di-(carboxymethylamino)-4-fluoro-triazin-6-yl, 2-sulphomethyl-methylamino-4-fluoro-triazin-6-yl, 2-β-cyanoethylamino-4-fluoro-triazin-6-yl, 2-benzylamino-4-fluoro-triazin-6yl, 2-β-phenyl ethylamino-4-fluoro-triazin-6-yl, 2-benzyl-methylamino-4-fluoro-triazin-6-yl, 2-(4'-sulphobenzyl)-amino4-fluoro-triazin-6-yl, 2-cyclohexylamino-4-fluoro-triazin-6-yl, 2-(o-, m- or p-methylphenyl)-amino4-fluoro-triazin-6-yl, 2-(o-, m- or p-sulphophenyl)-amino-4-fluoro-triazin-6-yl, 2-(2',5'-disulphophenyl)-amino4-fluorotriazin-6-yl, 2-(o-, m- or p-chlorophenyl)-amino-4-fluoro-triazin-6-yl, 2-(o-, m- or p-methoxyphenyl)-amino-4-fluoro-triazin-6-yl, 2-(2'-methyl-4'-sulphophenyl)-amino4-fluoro-triazin-6-yl, 2-(2'-methyl-5'-sulphophenyl)-amino-4-fluoro-triazin-6-yl, 2-(2'-chloro-4'-sulphophenyl)-amino-4-fluoro-triazin-6-yl, 2-(2'-chloro-5'-sulphophenyl)-amino-4-fluoro-triazin-6-yl, 2-(2'-methoxy-4'-sulphophenyl)-amino-4-fluoro-triazin-6-yl, 2-(o-, m- or p-carboxyphenyl)-amino-4-fluoro-triazin-6-yl, 2-(2',4'-disulphophenyl)-amino-4-fluoro-triazin-6-yl, 2-(3', 5'-disulphophenyl)-amino-4-fluoro-triazin-6-yl, 2-(2'-carboxy4'-sulphophenyl)-amino-4-fluoro-triazin-6-yl, 2-(2'-carboxy-5'-sulphophenyl)-amino-4-fluoro-triazin-6-yl, 2-(6'-sulpho-naphth-2'-yl)-amino-4-fluoro-triazin-6-yl, 2-(4',8'- disulphonaphth-2'-yl)-amino-4-fluoro-triazin-6-yl, 2-(6',8'-disulphonaphth-2'-yl)-amino-4-fluoro-triazin-6-yl, 2-(N-methyl-N-phenyl)-amino-4-fluoro-triazin-6-yl, 2-(N-ethyl-N-phenyl)-amino-4-fluoro-triazin-6-yl, 2-(N-β-hydroxyethyl-N-phenyl)-amino4-fluoro-triazin-6-yl, 2-(N-isopropyl-N-phenyl)-amino-4-fluoro-triazin-6-yl, 2-morpho- lino-4-fluoro-triazin-6-yl, 2-piperidino-4-fluoro-triazin-6-yl, 2-(4',6',8'-trisulphonaphth-2'-yl)-amino-4-fluorotriazin-6-yl, 2-(3',6',8'-trisulphonaphth-2'-yl)-amino-4-fluoro-triazin-6-yl, 2-(3', 6'-disulphonaphth- 1'-yl)-amino-4-fluoro-triazin-6-yl, N-methyl-N-(2,4-dichlorotriazin-6-yl)-carbamyl, N-methyl-N-(2-methylamino-4-chlorotriazin-6-yl)-carbamyl, N-methyl-N-(2-dimethylamino-4-chlorotriazin-6-yl)-carbamyl, N-methyl- or N-ethyl-N-(2,4-dichlorotriazin-6-yl)-aminoacetyl, 2-methoxy-4-fluoro-triazin-6-yl, 2-ethoxy-4-fluoro-triazin-6-yl, 2-phenoxy-4-fluoro-triazin-6-yl, 2-(o-, m- or p-sulphophenoxy)-4-fluoro-triazin-6-yl, 2-(o-, m- or p-methyl- or -methoxy-phenoxy)-4-fluoro-triazin-6-yl, 2-β-hydroxyethylmercapto-4-fluoro-triazin-6-yl, 2-phenylmercapto-4-fluoro-triazin-6-yl, 2-(4'-methylphenyl)-mercapto-4-fluorotriazin-6-yl, 2-(2',4'-dinitrophenyl)-mercapto-4-fluoro-triazin-6-yl, 2-methyl-4-fluoro-triazin-6-yl, 2-phenyl-4-fluoro-triazin-6-yl and the corresponding 4-chloro- and 4-bromotriazinyl radicals and the corresponding radicals obtainable by exchange of halogen with tertiary base, trimethylamine, triethylamine, dimethyl-β-hydroxyethylamine, triethanolamine, N,N-dimethylhydrazine, pyridine, α, β- or γ-picoline, nicotinic acid or isonicotinic acid, sulphinates, in particular benzenesulphonic acid, or hydrogen sulphite, and di- or trihalogenopyrimidinyl radicals, such as 2,4-dichloropyrimidin-6-yl, 2,4,5-trichloro-pyrimidin-6-yl, 4,5-dichloropyrimidin-6-yl, 2,4-difluoropyrimidin-6-yl, 4,5-difluoropyrimidin-6-yl, 4-fluoro-5-chloropyrimidin-6 -yl, 2,4-difluoro-5-chloropyrimidin-yl and 2,3-dichloroquinoxaline-5-carbonyl and 2,3-dichloroquinoxaline-6-carbonyl.

Suitable diazo components for the reactive dyestuffs of the formula (I) are, inter alia, those wherein D has the abovementioned meaning, and represents $D^2$ with the meaning given there, and furthermore represents reactive diazo components $D^3$, wherein $D^3$ denotes

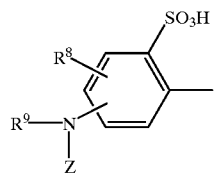

wherein $R^8$ can assume the meanings given for $R^1$ and additionally can denote $SO_3H$, $OSO_3H$ or $COOH$ and $R^9$ represents H, $T^1$ or $T^4$.

The dyestuffs according to the invention, in particular disperse dyestuffs of the formula (I), can be prepared by coupling diazotized amines which, as the amine, correspond to the formula (IV)

D-NH$_2$ (IV)

to coupling components of the

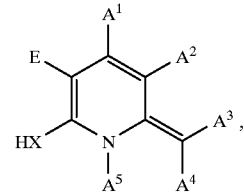

(V)

wherein $A^1$ to $A^5$, D and X have the abovementioned meaning and

E represents a substituent which can be replaced by electrophilic substitution, such as, for example, H, $-CO_2H$, $-CH_2OH$, $-SO_3H$, $-CH=O$, $-COT$,

Such a coupling process with displacement of a substituent is described, for example, in GB 2 036 775 and Jp 58 157 863.

The coupling can be carried out in an aqueous and non-aqueous solvent. Non-aqueous solvents which may be mentioned are alcohols, such as methanol, ethanol, propanol, butanol, pentanol and the like, dipolar aprotic solvents, such as DMF, DMSO and NMP, and water-immiscible solvents, such as toluene and chlorobenzene.

The coupling is preferably carried out in the stoichiometric ratio, but it may be advantageous and in some cases appropriate for economic reasons to employ the cheaper components in an excess of up to 30%.

The coupling is carried out at temperatures between −30 and 100° C., temperatures from −10 to 30° C. being preferred and temperatures from −5 to 10° C. being particularly preferred.

The coupling can be carried out in an acid medium and also in an alkaline medium. pH values >0.5 and <14 are preferred, particularly preferably >1.0 and <12 and especially preferably >3.0 and ≦11.0.

An oxidative coupling of (hetero)aromatic hydrazines of the formula (VI)

D-NH-NH$_2$ (VI)

to coupling components of the formula (V) is furthermore also possible, which is characterized in that VI is coupled oxidatively in the presence of V. Methods of oxidative coupling are described, for example, in Houben-Weyl "Methoden der organischen Chemie [Methods of organic chemistry]", Volume 10/3, page 360 et seq., and also in EP 201 892 or Chem. Express 1988, 3(7), 423–6.

A process for the preparation of dyestuffs of the formula (I) wherein X denotes O is furthermore preferred, which is characterized in that compounds of the formula (VII), which can exist in the tautomeric forms of the formula (VIIa) and (VIIb)

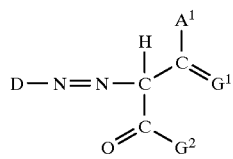

(VIIa)

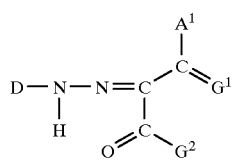

(VIIb)

wherein
$G^1$ denotes O, NH or NT, preferably O,
$G^2$ represents -OT, -NH$_2$ or -NHT, preferably $OT^1$, and
D and $A^1$ have the abovementioned meanings,
are subjected to a condensation reaction with enamines of the formula (VIII)

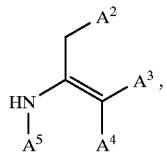

(VIII)

wherein $A^2$ to $A^5$ have the abovementioned meanings.

This condensation reaction is preferably carried out, in the case of the disperse dyestuffs of the formula (I), in organic solvents, in particular dipolar aprotic solvents. Examples which may be mentioned are alcohols, such as methanol and ethanol, and, on the other hand, DMF, DMSO and NMP.

The condensation reaction is carried out at temperatures from −10 to 200° C., preferably from 0 to 150° C., in particular at 20 to 130° C.

The condensation reaction is preferably carried out in the presence of bases, such as, for example, secondary and tertiary amines and alkali metal alcoholates. The amount of base varies here between catalytic and five times the molar amounts. 1 to 3 mol of base are preferably employed. Suitable bases are, for example, triethylamine, sodium methylate, sodium ethylate, sodium butylate, sodium amylate, K$_2$CO$_3$, Na$_2$CO$_3$, DBU (diazabicycloundecene) and DBN (diazabicyclononene).

The compounds of the formula (VII) are known in some cases from DE-A-2 015 172, or they can be prepared by known methods.

The enamines of the formula (VIII) are known in most cases and/or are accessible by "dimerization" or "codimerization" of cyanoacetic acid derivatives in accordance with the equation

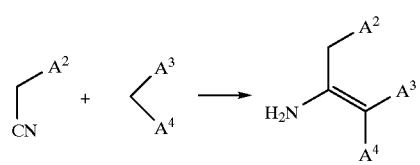

cf., for example, Liebigs Ann. Chem. 1987, 1131 to 1132 and literature cited therein.

Preferred enamines of the formula (VIII) correspond to the formulae (VIIIa) to (VIIIc).

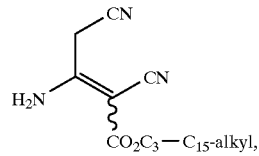

(VIIIa)

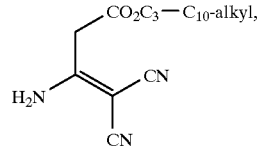

(VIIIb)

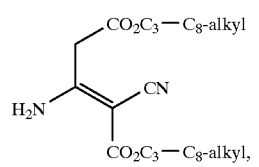

(VIIIc)

Another method of preparation of enamines of the formula (VIII) is the reaction of iminoesters with methyleneactive compounds in accordance with Liebigs Ann. Chem. 1986, 533 to 544

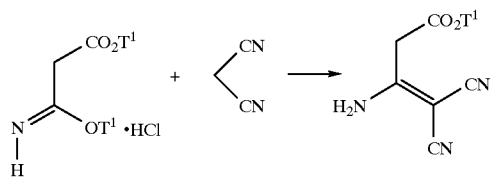

wherein $T^1$ has the abovementioned meaning.

Compounds of the formula (V) are known in some cases from AU 491 554, Aust. J. Chem. 29 (1976), 1039–50 and J. Am. Chem. Soc. 81, 2452.

The invention furthermore relates to compounds of the formula (V)

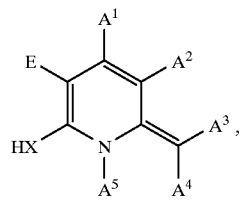

(V)

wherein
E and X have the abovementioned broadest meanings,
$A^1$ and $A^2$ independently of one another denote H or a radical of the formula T, -COH, -CO-T, -CO$_2$T, -CN, -CONH$_2$, -CONHT, -CONT$_2$, CF$_3$, -NO$_2$, NO, -SO$_2$T, -OH, -OT, -OCOT, -OCO$_2$T, -OSO$_2$T, Cl, Br or I,
wherein
T can assume the meaning of $T^1$, $T^2$, $T^3$, $T^4$ or $T^5$, where
$T^1$=alkyl, cycloalkyl or aralkyl,
$T^2$=alkenyl,
$T^3$=alkinyl, $T^4$ = aryl, $T^5$ = hetaryl, $A^3$ and $A^4$ independently of one another denote an electron-withdrawing radical, or together with the common C atom form a cyclic methylene-active compound, $A^5$ represents H or a radical of the formula T, $-OT^1$, $-NH_2$, $-NHT$, $-NT_2$, $-NHCOH$, $-NHCOT$, $-N=CH-T$, $-N=CT_2$ or $NHSO_2T$, or $A^1$ and $A^2$ or $A^2$ and $A^3$, together with the particular atoms in between, form an unsaturated, optionally substituted 5- or 6-membered carbo- or heterocyclic radical, where, in the case of ring formation with participation of one of the radicals $A^3$ or $A^4$, the other particular radical denotes an electron-withdrawing radical, and where the radicals $A^1$ to $A^5$ optionally carry one or more $SO_3H$, COOH or $K^\oplus$ and $B^\ominus$ groups, wherein $K^\oplus$ and $B^\ominus$ have the above meanings.

Preferred compounds of the formula (V) are those wherein $A^1$ denotes H, $T^1$, $T^4$ or $CF_3$, $A^2$ denotes H, $-CO_2T^1$, $-CN$, $-CONH_2$, $-CONHT$, $-CO_2T^2$ or $-CONT^1_2$, $A^3$ denotes $-CO_2T^1$, $-CN$, $-CONH_2$, $-CONHT$, $-CONT^1_2$ or $-CO_2T^2$, $A^4$ denotes $-CO_2T^1$, $-CN$, $-CONH_2$, $-CONHT$, $-CONT^1_2$ or $-CO_2T^2$, $A^5$ denotes H, $T^1$ or $T^2$ or $A^3$ and $A^4$, together with the common C atom, denote a cyclic methylene-active compound of the formula (IIa) or (IId) and E denotes H.

Particularly preferred compounds of the formula (V) are those wherein $A^1$ denotes H, $CH_3$, $C_6H_5$ or $CF_3$, $A^2$ denotes H, $CO_2C_1$-$C_{10}$-alkyl, $-CO_2C_2$-$C_{10}$-alkenyl, $A^3$ and $A^4$ independently of one another denote $-CO_2C_1$-$C_{10}$-alkyl, $-CO_2C_2$-$C_{10}$-alkenyl or $-CN$, $A^5$ denotes H or $C_1$-$C_{10}$-alkyl and E denotes H.

The invention furthermore relates to a process for the preparation of the compounds of the formula (V) in the form of the compound Va or Vb, wherein X represents O or NH, characterized in that acetic acid derivatives of the formula IXa or IXb are reacted with enamines of the formula (VIII):

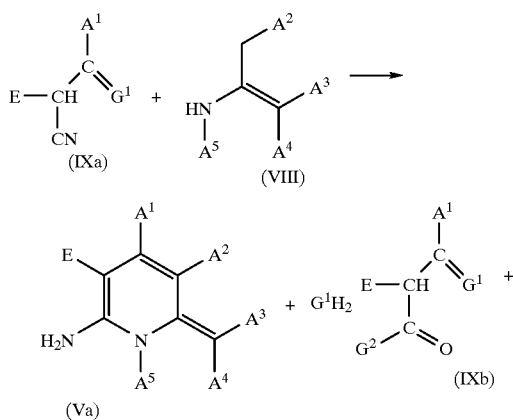

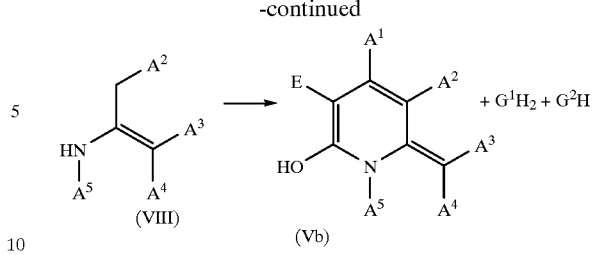

wherein $A^1$ to $A^5$, E, $G^1$ and X have the abovementioned broadest meaning, wherein $A^5$ preferably represents H, and $G^2$ has the abovementioned meaning.

Preferably, $G^1$ represents O,

E represents H and $G^2$ represents $OT^1$.

The reaction is preferably carried out in organic solvents. Suitable solvents are alcohols, dipolar aprotic solvents, such as DMF, water-immiscible solvents and esters, above all acylacetic esters, such as, for example, methyl or ethylacetoacetate.

Water-immiscible solvents offer the advantage that the water formed in the reaction in the case where $G^1=O$ can be removed azeotropically with them from the reaction mixture.

A particularly preferred embodiment, especially in the case of less reactive enamines of the formula (VIII), i.e. wherein $A^2$ represents $-CO_2T$, comprises working with an excess of (IX) as the solvent—without using further cosolvents. This excess of (IX) over (VIII) is preferably 5 to 500% by weight.

The reaction is preferably carried out at temperatures from 0 to 200° C., preferably 20 to 150° C., particularly preferably at 70 to 120° C.

The reaction can be accelerated by catalysts. Suitable catalysts are acids, such as, for example, glacial acetic acid, and acid-base pairs, such as β-alanine-glacial acetic acid, ammonium acetate, piperidine-glacial acetic acid and morpholine-glacial acetic acid.

Inorganic and organic bases are furthermore suitable as catalysts or reaction partners. Bases which may be mentioned are sodium hydroxide, sodium ethylate, potassium ethylate, triethylamine, piperidine, morpholine and ethanolamine, such as are also employed in condensation reactions of CH-acid compounds with acetylacetone and the like. (Compare: Monatshefte für Chemie 95 1201, 1473 (1964) and J. Chem. Eng. Data 29, 101).

Particularly suitable bases, especially with less reactive enamines of the formula (VIII), wherein $A^2$ represents $-CO_2T$, are sterically hindered strong bases, such as, for example, potassium tert-butylate, and sterically hindered N bases, such as, for example, diazabicycloundecene (DBU) and diazabicyclononene (DBN).

The reaction can be carried out under normal pressure and also under increased or reduced pressure. It is preferable, especially in the case of less reactive enamines of the formula (VIII), to work under reduced pressure under pressures of <200 mbar, in particular <100 mbar, so that the cleavage products water and alcohol formed from the condensation reaction with the preferred acetic acid derivative of the formula (IX), the alkylacetoacetate, can be removed rapidly from the reaction mixture.

In contrast to the acid catalysts and acid-base pairs, bases are preferably employed in the stoichiometric ratio or in an excess. The excess can be 1 to 500%.

A process which is also preferred is a process for the preparation of compounds of the formula V which correspond to the formula X which is characterized in that a trifluoroacetic ester of the formula (XI), which represents a particular embodiment of the acetic acid derivative of the formula (IX), is subjected to a condensation reaction with dimeric cyanoacetic acid esters of the formula (XII), which represent a particular embodiment of the enamines of the formula (VIII)

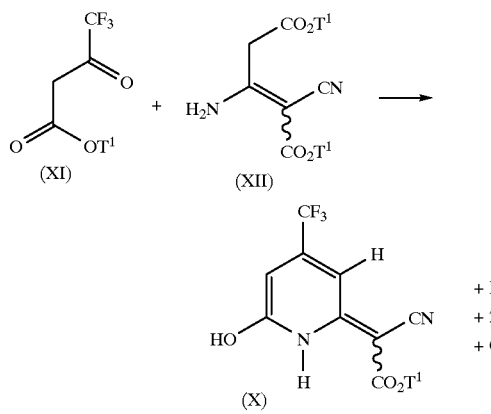

wherein $T^1$ has the abovementioned broadest meaning. The reaction conditions are the same as those described above for less reactive enamines.

The invention also relates to a process for the preparation of compounds of the formula (V), wherein $A^5$ represents $T^1$, $T^2$ or $T^3$, which is characterized in that pyridinium salts of the formula (XIII)

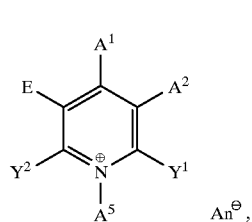

wherein
E, $A^1$ and $A^2$ have the abovementioned broadest meaning,
$An^\ominus$ is an anion, which can assume, for example, the meanings given for $B^\ominus$, and in particular represents $Cl^\ominus$, $Br^\ominus$, $I^\ominus$, $T^1OSO_3^\ominus$ or $TSO_3^\ominus$,
$A^5$ represents $T^1$, $T^2$ or $T^3$ and
$Y^1$ and $Y^2$ independently of one another represent a leaving group, such as F, Cl, Br, I, $-OSO_2T$, $-OT$, $-ST$ or $-SO_2T$,
are reacted with compounds of the formula (II)

wherein $A^3$ and $A^4$ have the abovementioned broadest meaning, to give compounds of the formula (XIV)

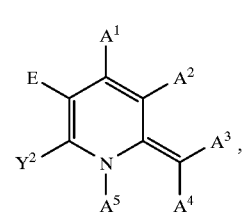

and these are reacted with compounds of the formula (XV)

$$XH_2 \qquad (XV)$$

wherein
X represents O, NH, $NT^1$, NCOT, $NCO_2T$ or $NSO_2T$,
to give compounds of the formula (V)
wherein $A^5$ represents $T^1$, $T^2$ or $T^3$.
In a preferred embodiment of this process,
E represents H,
$A^1$ represents H or $T^1$,
$A^2$ represents H,
$Y^1$ represents Cl, Br or I,
$Y^2$ represents Cl, Br, I or $-OT^1$ and
$H_2X$ represents $H_2O$, $NH_3$, $H_2NT^1$ or $H_2NSO_2T$, in particular $H_2O$.

In a particular embodiment of the process, $A^5$ represents $T^1$ or $T^2$, particularly preferably $T^1$, and especially preferably methyl or ethyl.

The reaction of the compounds of the formulae (XIII) and (II) can be carried out in water or in aqueous or non-aqueous solvents, such as, for example, alcohols or dipolar aprotic solvents.

Suitable temperatures are −20 to 150° C., preferably 0 to 100° C., in particular 15 to 80° C.

This reaction is preferably carried out in the presence of inorganic or organic bases. Suitable bases are alkali metal hydroxides, alkali metal alcoholates, alkali metal hydrides, alkali metal oxides, alkaline earth metal oxides, alkali metal carbonates, alkali metal bicarbonates, alkali metal hydrides or organic N bases, such as tertiary amine (triethylamine, DBU, DBN and the like). These bases are preferably employed in stoichiometric amounts, i.e. twice the molar amounts in (XIII).

Instead of the compound (II), the corresponding anion of (II)

$$\overset{\ominus}{C}H\diagup^{A^3}_{\diagdown A^4} \quad Cat^\oplus, \qquad (II.1)$$

wherein $A^3$ and $A^4$ have the abovementioned broadest meaning and $Cat^\oplus$ represents a cation, such as, for example, those of lithium, sodium and potassium, can also be employed for the reaction with pyridinium salts (XIII).

The second reaction stage—conversion of (XIV) into (V)—is also preferably carried out in the presence of bases.

In the case where the compounds of the formula (XV) correspond to the amines $-NH_3$ or $H_2NT^1$, these reactants are also preferably employed simultaneously as the base and, where appropriate, also as the solvent.

If X represents O, alkali metal hydroxides, alkaline earth metal hydroxides and/or alkali metal carbonates are preferably employed as bases.

If X represents -NCOT, -NCO$_2$T or -NSO$_2$T, the corresponding anion, for example C$_6$H$_5$SO$_2$NH$^\ominus$, is preferably employed as the base and reactant.

Further preferred bases here are also inert bases and sterically hindered bases. Suitable bases are, for example, tertiary amines, such as triethylamine, DBU and DBN. Preferably, at least 2 molar equivalents of base are employed.

Suitable solvents are preferably organic solvents which are inert under these conditions, such as, for example, dipolar aprotic solvents, aromatic hydrocarbons, such as toluene, and chlorinated hydrocarbons, such as chlorobenzene.

Depending on the nucleophilicity of the educt H$_2$X or of the corresponding base, the reaction takes place at temperatures between −20° C. and 200° C., preferably 0° C. and 150° C.

The pyridinium salts of the formula (XIII)* required are accessible in a simple manner by quaternization of corresponding pyridines (XVI) with alkylating agents A$^5$-An, such as, for example, dimethyl sulphate, in accordance with the reaction

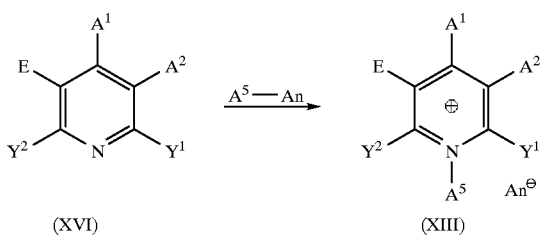

(XVI)                  (XIII)

For ecological and economic reasons, the quaternization and also the reaction with compounds (II) and, where appropriate, also the reaction with XH$_2$ are preferably carried out without intermediate isolation.

Another process for the preparation of the coupling components of the formula (V), wherein A$^5$ represents T, is characterized in that pyridine derivatives of the formula (XVII) are reacted with compounds of the formula (II):

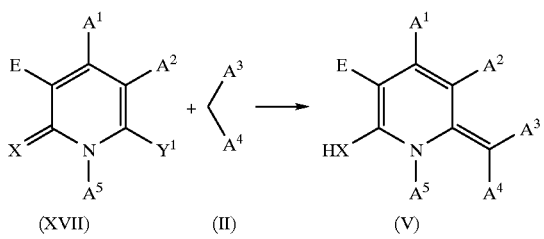

(XVII)        (II)        (V)

wherein X=O, A$^1$ to A$^4$ and E have the abovementioned meaning and A$^5$ represents T.

In a preferred embodiment of this process, E represents H,
A$^1$ represents H or T$^1$, especially preferably H,
A$^2$ represents H,
Y$^1$ represents F, Cl, Br, I, OSO$_2$T, SO$_2$T, -ST or OT, particularly preferably Cl, Br or -SO$_2$T, and especially preferably Cl, and
A$^5$ represents T$^1$ or T$^2$, particularly preferably T$^1$, and especially preferably methyl or ethyl, and
one of the two radicals A$^3$ and A$^4$ preferably represent -CN, -CO$_2$T, -CONH$_2$, -CONHT, -CONT$^2$, -CHO, -COT, -SO$_2$T, -SO$_2$NH$_2$, -SO$_2$NHT, -SO$_2$NT$_2$, -NO$_2$, T$^4$ or T$^5$, while the other preferably represents -CN, -CO$_2$T, -CONH$_2$, -CONHT or -CONT$^2$, or A$^3$ and A$^4$, together with the C atom to which they are bonded, form a cyclic methylene-active compound of the formulae (IIa to IIv), preferably (IIa to IIh), in particular (IIa and IId).

Suitable solvents for this reaction are preferably organic solvents. Both water-miscible and water-immiscible solvents are possible here.

The reaction temperatures are preferably in the range from 20 to 250° C., preferably 50 to 150° C.

Bases are preferably added, in particular more than 2 molar equivalents of base, based on the starting material of the formula (XVII).

Suitable bases are inorganic or organic in nature. For example, tertiary amines, such as triethylamine, DBU and DBN, are suitable.

Another process for the preparation of coupling components of the formula (V), which correspond to the formula (XX), wherein A$^5$ represents T$^1$, T$^2$ or T$^3$, is characterized in that 2-methylpyridones of the formula (XVIII) are reacted with phthalic acid esters of the formula (XIX) in the presence of bases

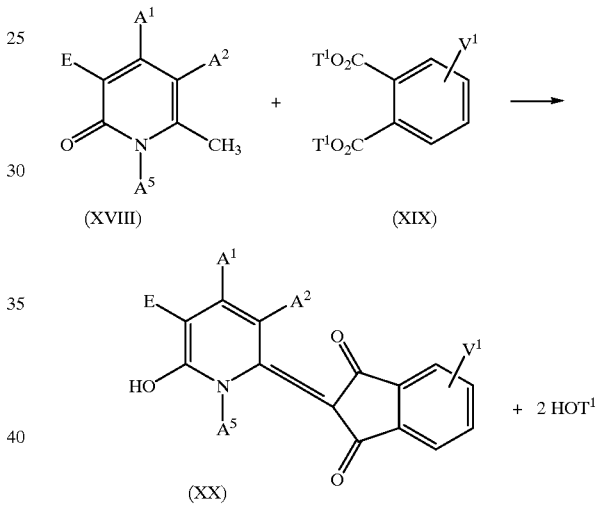

wherein A$^1$, A$^2$, E, T$^1$ and V$^1$ have the abovementioned broadest meaning.

In a preferred embodiment of this process
E represents H,
A$^5$ represents T$^1$, particularly preferably methyl or ethyl,
A$^1$ represents H, T$^1$ or T$^4$, particularly preferably T$^1$, and especially preferably methyl, and
V$^1$ represents H.

In this reaction, the phthalic acid ester of the formula (XIX) simultaneously serves as the solvent.

Suitable bases are preferably alkali metal alcoholates, which are preferably employed in at least equimolar amounts, based on (XVIII).

The reaction temperature is in general 50 to 200° C., preferably 100 to 160° C., the alcohol T$^1$OH formed preferably being distilled off from the reaction.

The removal of the alcohol can be promoted by working under reduced pressure.

The product can be isolated in crystalline form by discharging the mixture onto water and acidifying the aqueous phase.

The dyestuffs of the formula (I) according to the invention are suitable, depending on the presence of substrate-specific substituents, for dyeing and printing naturally occurring and synthetic materials, such as, for example, cellulose fibres, cotton, wool, silk, polyamide, polyacrylonitrile, polyester or polyolefins.

Thus, for example, the dyestuffs described as disperse dyestuffs of the formula (I) are particularly suitable, either as such or also as a mixture with other disperse dyestuffs, for dyeing and printing hydrophobic synthetic fibre materials and mixtures thereof with naturally occurring fibre materials.

Possible hydrophobic synthetic materials are, for example: cellulose 2½-acetate, cellulose triacetate, polyamides and, in particular, polyesters, such as, for example, polyethylene glycol terephthalate. Mixtures thereof with naturally occurring fibre materials are, for example, cotton, regenerated cellulose fibres or wool.

They are furthermore suitable for dyeing and, where appropriate, printing waxes, oils and plastics such as polymethacrylate, PVC, polystyrene or ABS.

They are also suitable for textile and non-textile thermotransfer printing, for example by means of a thermal head or also by means of ink-jet processes.

The compounds described as cationic dyestuffs of the formula (I) in the context of this Application are preferably used for dyeing or printing acid-modified polyester or polyamide, but preferably for dyeing and printing polyacrylonitrile.

Moreover, they can also be employed for dyeing paper.

The compounds described as reactive dyestuffs of the formula (I) in the context of this Application are preferably used for dyeing and printing materials containing hydroxyl groups, such as, for example, cellulose fibres, in particular cotton, and for dyeing and printing materials containing amide groups, such as, for example, wool, silk and polyamide.

The compounds described as acid dyestuffs of the formula (I) in the context of this Application are preferably employed for dyeing and printing naturally occurring or synthetic polyamide and base-modified polyacrylonitrile fibres. They can moreover be employed for dyeing paper.

The dyestuffs can be applied here from aqueous or non-aqueous liquors or also in printing processes.

They produce strong dyeings with good general fastnesses.

Neutral dyestuffs produce particularly brilliant dyeings of high fastness to light on polyester. The shades range here from yellow to blue, the particular strength lying in brilliant red shades.

If $A^3$ and $A^4$ in the formulae mentioned in the Examples have different meanings, the configuration on the carbon atom to which they are bonded is not intended to be specified by the formulae. The enamines 3-amino-2-cyano-pentene-dioic acid diesters (Δ2-amino-1-cyanoglutaconic acid diesters) used in the Examples were prepared by processes analogous to that described in Liebigs Anm. Chem. 1987, 1131, in which such enamines are described as having the Z configuration.

EXAMPLES

Example 1

Preparation of the dyestuff of the formula

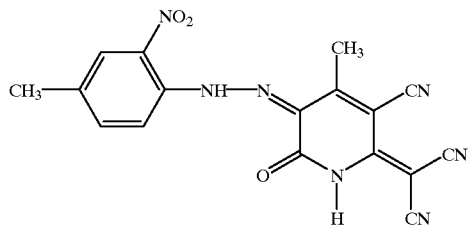

5.5 ml of 40% strength nitrosylsulphuric acid were added to 6.1 g of 4-methyl-2-nitroaniline, dissolved in 20 ml of propionic acid and 40 ml of glacial acetic acid, at 0–5° C. in the course of 10 minutes. The mixture was stirred at 0–5° C. for a further 2 hours. 20 ml of 10% strength aqueous amidosulphonic acid solution and then, at 5° C., the above diazotization reaction mixture were added to a solution, brought to pH 7 by means of a few ml of concentrated sodium hydroxide solution, of 5.8 g of [6-hydroxy-3-cyano-4-methyl-2(1H)-pyridinylidene]-malononitrile in 400 ml of water. The mixture was allowed to warm to room temperature in the course of 16 hours, the precipitate was filtered off with suction and the filter cake was washed neutral with water.

Yield: 9.3 g

MS, m/z (%): 361 (72) [M$^+$·], 315 (18) [M$^+$·—NO$_2$] 152 (100)

UV (DMF): $\lambda_{max}$=537 nm

The dyestuff dyes polyester in a bluish-tinged red with good fastness properties.

The dyestuffs of the formula

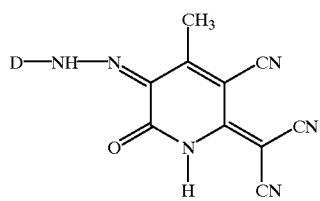

listed below, which likewise dye polyester with good properties, were obtained analogously to Example 1.

TABLE 1

| Ex. No. | D | $\lambda_{max}$ nm | Colour shade on polyester |
|---|---|---|---|
| 2 | 4-methoxy-2-nitrotoluene (H₃CO-, -NO₂ on tolyl) | 535 (CH₃CN) | Ruby |
| 3 | 4-ethoxy-2-nitrotoluene (C₂H₅-O-, -NO₂ on tolyl) | 535 (CH₃CN) | Ruby |
| 4 | 4-chloro-2-nitrotoluene (Cl-, -NO₂ on tolyl) | | Yellowish-tinged red |
| 5 | 2-nitrotoluene | | Yellowish-tinged red |
| 6 | 3-chloro-4-methyl-nitrobenzene (O₂N-, -Cl on tolyl) | | Yellowish-tinged red |
| 7 | 2-methoxy-4-nitrotoluene (O₂N-, -OCH₃ on tolyl) | 536 (CH₃CN) | bluish-tinged pink |
| 8 | 2-methyl-4-nitrotoluene (O₂N-, -CH₃ on tolyl) | | Bluish-tinged red |
| 9 | 4-methoxy-3-methyl-nitrobenzene (O₂N-, -OCH₃, -CH₃) | | Bluish-tinged red |
| 10 | 2-ethoxytoluene (-OC₂H₅ on tolyl) | 518 546 sh (CH₃CN) | Ruby |
| 11 | 2,4-dimethyltoluene (CH₃-, -CH₃ on tolyl) | | Bluish-tinged red |

TABLE 1-continued

| Ex. No. | D | $\lambda_{max}$ nm | Colour shade on polyester |
|---|---|---|---|
| 12 | 2-chlorophenyl | | Bluish-tinged scarlet |
| 13 | 4-cyclohexyl-2,3-dimethylphenyl (H on cyclohexyl) | | Bluish-tinged red |
| 14 | 2-(CO$_2$C$_6$H$_{13}$)phenyl | | Scarlet |
| 15 | 3-(CO$_2$C$_5$H$_{11}$)phenyl | | Yellowish-tinged red |
| 16 | 4-(CO$_2$C$_8$H$_{17}$)phenyl | | Yellowish-tinged red |
| 17 | 2,4-dimethoxyphenyl | | Violet |
| 18 | 2-fluorophenyl | 494, 516 sh (CH$_3$CN) | Yellowish-tinged red |
| 19 | 2-(OC$_4$H$_9$)phenyl | 518, 546 sh (CH$_3$CN) | Bluish-tinged red |
| 20 | 4-methyl-2-(OC$_2$H$_5$)phenyl | | Red-violet |

TABLE 1-continued

| Ex. No. | D | $\lambda_{max}$ nm | Colour shade on polyester |
|---|---|---|---|
| 21 | 4-ethoxy-2-methylphenyl with OC$_2$H$_5$ at position 1 (2,5-diethoxy with methyl) — ring: C$_2$H$_5$O— and —OC$_2$H$_5$, with CH$_3$ | | Reddish-tinged violet |
| 22 | 4-chloro-2-methylphenyl-O-(4-chlorophenyl) | 507 (CH$_3$CN) | Bluish-tinged red |
| 23 | 2-methylphenyl with OC$_8$H$_{17}$ | 518, 546 sh (CH$_3$CN) | Bluish-tinged red |
| 24 | 2-methylphenyl with OC$_6$H$_{13}$ | 518, 546 sh (CH$_3$CN) | Bluish-tinged red |
| 25 | 4-ethoxy-3-chloro-2-methylphenyl (C$_2$H$_5$O—, Cl) | | Red-violet |
| 26 | 4-butyl-3-bromo-2-methylphenyl (C$_4$H$_9$, Br) | 507, 531 sh (CH$_3$CN) | Bluish-tinged red |
| 27 | 4-butoxy-2-methylphenyl (C$_4$H$_9$O—) | | Red-violet |
| 28 | 2-benzothiazolyl | 535 (CH$_3$CN) | Ruby |
| 29 | 2-methylphenyl-O-(4-ethoxycarbonylphenyl) (—CO$_2$C$_2$H$_5$) | | Bluish-tinged red |

TABLE 1-continued

| Ex. No. | D | $\lambda_{max}$ nm | Colour shade on polyester |
|---|---|---|---|
| 30 | C₄H₉—⟨phenyl⟩— | | Bluish-tinged red |

Example 31

Preparation of [6-hydroxy-3-cyano4-methyl-2-(1H)-pyridinylidene]malononitrile 15.4 g of the sodium salt of 2-amino-1,2,3-tricyanopropene ("malononitrile dimer") were heated at the boil under reflux with 13 g of ethyl acetoacetate, 1 ml of piperidine and 6 g of glacial acetic acid in 100 ml of ethanol for 16 hours. After cooling, a beige powder was filtered off with suction and washed with ethanol.

Yield: 14.5 g

IR ν (cm$^{-1}$): 3430, 2185 (C≡N), 2205(C≡N), 2225(C≡N) 1668, 1566, 1356, 832

$^1$H-NMR (d$_6$-DMSO, 300 MHz, ppm): δ=2.15 (s, 3H, CH$_3$), 5.70 (s, 1H), 7.30 (s, 2H, OH, NH)

MS, m/z (%): 198 (42 [M$^{+\cdot}$], 170 (13) [M$^{+\cdot}$—H$_2$O] 155 (100)

Example 32

Preparation of the dyestuff of the formula 8.3 ml of 40% strength nitrosylsulphuric acid were added to 6.6 g of methyl 2-aminobenzoate, dissolved in 15 ml of propionic acid and 30 ml of glacial acetic acid, at 0–5° C. in the course of 10 minutes. The mixture was stirred at 0° C. for a further 2 hours.

70 ml of the solution, described in the following Example No. 33, of the coupling component ethyl [6-hydroxy4-methyl-3-(ethoxycarbonyl)-2(1H)-pyridinylidene]-cyanoacetate (about 0.5 mol) in 550 ml of dimethylformamide were topped up to 200 ml with ethanol, 2 g of amidosulphonic acid were added and coupling was then carried out with the above diazotization mixture at 0° C., with the addition of 50 g of ice. The mixture was subsequently stirred for 15 hours and the product was filtered off with suction and washed with water.

Yield: 15.3 g. After recrystallization from dimethylformamide, 6.3 g remained.

The dyestuff dyed polyester in a brilliant orange with good fastness properties.

MS, m/z (%): 454 (100) [M$^{+\cdot}$], 422 (8) 409 (8), 350 (25), 349 (16), 322 (25) 293 (18)

$\lambda_{max}$: 483 nm (CH$_3$CN)

Example 33

Preparation of coupling component of the formula

A solution of 113 g of diethyl 3-amino-2-cyano-pentenedioate ("dimeric ethyl cyanoacetate", 0.5 mol), 90 ml of ethyl acetoacetate and 76 g of diazabicycloundecene (DBU) in 500 ml of dimethylformamide was stirred at 120° C. for 11 hours. A further 25 ml of ethyl acetoacetate were added and the mixture was stirred at 120° C. for a further 9 hours, the readily volatile cleavage products being distilled off. The mixture was topped up to a volume of 800 ml with 50 ml of dimethylformamide and the brown solution was employed directly for the coupling reaction. A sample was freed from the solvent under 20 mbar/100° C. The brown oil which remained showed the following mass spectrum:

MS, m/z (%): 292 (27) [M$^{+\cdot}$], 247 (14), 218 (27), 192 (42), 174 (58), 164 (35), 152 (65), 151 (51), 148 (43), 96 (33), 42 (64), 29 (100)

The dyestuffs of the formula listed below (Table 2), which likewise dye polyester with good fastness properties, were obtained analogously to Example 32.

TABLE 2

| Ex. No. | D | $\lambda_{max}$ nm | Colour shade on polyester |
|---|---|---|---|
| 34 | 2-nitro-4-methoxy-toluene (CH₃O-, -NO₂) | 507 (DMF) | Bluish-tinged red |
| 35 | 2-nitro-4-ethoxy-toluene (C₂H₅O-, -NO₂) | 515 (CH₃CN) | Bluish-tinged red |
| 36 | 4-methyl-toluene (CH₃-) | | Scarlet |
| 37 | 2-nitro-4-methyl-toluene (CH₃-, -NO₂) | 495 (CH₃CN) | Scarlet |
| 38 | 2-nitro-toluene (-NO₂) | | Orange |
| 39 | 4-(ethoxycarbonyl)-toluene (C₂H₅O₂C-) | 483 (CH₃CN) | Orange |
| 40 | 3,4-dichloro-toluene (Cl, Cl) | | Orange |
| 41 | 2,4-dichloro-toluene (Cl, Cl) | | Orange |
| 42 | 2-bromo-4-ethoxy-toluene (C₂H₅O-, -Br) | 507 (CH₃CN) | Pink |
| 43 | 2-chloro-4-ethoxy-toluene (C₂H₅O-, -Cl) | 507 (CH₃CN) | Bluish-tinged red |

TABLE 2-continued

| Ex. No. | D | $\lambda_{max}$ nm | Colour shade on polyester |
|---|---|---|---|
| 44 | ![CH3, Br substituted benzene] | | Scarlet |
| 45 | ![CH3-CO-NH-, CF3, CH3 substituted benzene] | | Red |

Example 46

Preparation of the dyestuff mixture of the formula

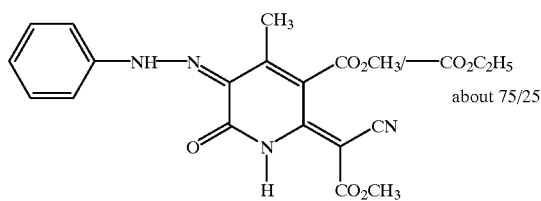
about 75/25

11.7 g of ethyl 2-phenylazo-acetoacetate and 11 g of the sodium salt of dimethyl 3-amino-2-cyano-pentenedioate ("dimeric methylcyanoacetate") were stirred in 50 ml of dimethylformamide at 90° C. for 10 hours. After addition of a further 2.2 g of dimeric methylcyanoacetate, the mixture was heated at 100° C. for a further 6 hours. After cooling to room temperature, 100 ml of methanol, 6 g of 30% strength hydrochloric acid and 15 ml of water were added. The product was filtered off with suction and washed with methanol.

Yield: 4.1 g

The dyestuff dyed polyester in a brilliant scarlet with good fastness properties.

MS, m/z (%) 382 (22) [M$^{+\cdot}$ ethyl ester] 369 (20), 368 (89) [M$^{+\cdot}$ methyl ester], 337 (9) [M$^{+\cdot}$ methyl ester - OCH$_3$], 310 (9), 276 (7), 231 (19), 199 (11), 105 (19) 93 (30), 92 (28), 77 (100)

$\lambda_{max}$: 486 nm (CH$_3$CN)

The following dyestuffs of the formula

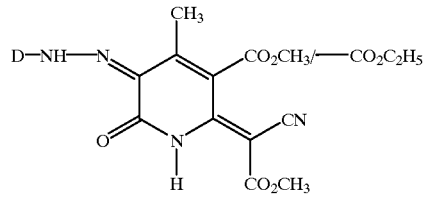

which likewise dye polyester with good fastness properties, were obtained analogously to Example 46.

TABLE 3

| Ex. No. | D | $\lambda_{max}$ nm | Colour shade on polyester |
|---|---|---|---|
| 47 | ![OCH3, CH3 substituted benzene] | | Ruby |
| 48 | ![C2H5O-, CH3 substituted benzene] | | Bluish-tinged red |
| 49 | ![OCH3, O2N-, CH3 substituted benzene] | 512 (CH$_3$CN) | Red |

TABLE 3-continued

| Ex. No. | D | $\lambda_{max}$ nm | Colour shade on polyester |
|---|---|---|---|
| 50 | 2-methylphenyl phenyl ether | 498 (CH$_3$CN) | Scarlet |
| 51 | 2-chloro-methylbenzene | 485 (CH$_3$CN) | Orange |
| 52 | 2-methyl-5-methyl-nitrobenzene (H$_3$C-, O$_2$N-) | | Orange |
| 53 | 4-methoxy-3-methyl-nitrobenzene (OCH$_3$, O$_2$N-) | 512 (CH$_3$CN) | Red |
| 54 | phenyl-N=N-tolyl | | Bluish-tinged red |
| 55 | 2-nitro-4-methoxy-toluene (NO$_2$, CH$_3$O-) | 515 (CH$_3$CN) | Bluish-tinged red |
| 56 | 2-nitro-4-ethoxy-toluene (NO$_2$, C$_2$H$_5$O-) | 516 (CH$_3$CN) | Bluish-tinged red |
| 57 | 2-methyl-benzoate methyl (CO$_2$CH$_3$) | 483 (CH$_3$CN) | Orange |
| 58 | 2-methyl-benzoate ethyl (CO$_2$C$_2$H$_5$) | 483 (CH$_3$CN) | Orange |

TABLE 3-continued

| Ex. No. | D | $\lambda_{max}$ nm | Colour shade on polyester |
|---------|---|---------------------|---------------------------|
| 59 | 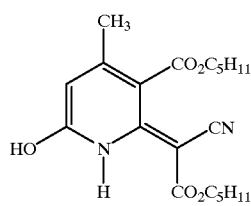 | 483 (CH₃CN) | Orange |

Example 60

Preparation of the coupling component of the formula

CH₃
CO₂C₅H₁₁
HO
N
H
CN
CO₂C₅H₁₁

Diamyl 3-amino2-cyano-pentenedioate ("dimeric amylcyanoacetate") was prepared analogously to Junek, Monatschefte für Chemie, 101 [1979] 1208.

12.2 ml of diazabicyclononene (DBN) and 34.4 g of amyl acetoacetate were added to 31 g of diamyl 3-amino2-cyano-pentenedioate and the mixture was heated at 80° C. for 4 hours A further 8.6 g of amylacetoacetate were added and the mixture was heated at 80° C. for a further 2 hours. A brown oil was obtained which, when taken up in 200 ml of N-methylpyrrolidone, gave a weight of 276 g and was employed directly for the coupling reaction was obtained. A sample which was concentrated under 0.5 mbar/100° C. gave the following mass spectrum MS, m/z (%) 376 (12) [M⁺], 262 (8), 236 (11), 219 (18), 218 (21), 193 (11), 192 (45), 151 (30), 55 (35), 43 (100)

The dyestuffs listed below, which likewise dyed polyester with good fastness properties, were obtained by a coupling reaction analogously to Example 32.

TABLE 4

CH₃
D—NH—N
CO₂C₅H₁₁
O     N     CN
      H     CO₂C₅H₁₁

| Ex. No. | D | $\lambda_{max}$ nm | Colour shade on polyester |
|---------|---|---------------------|---------------------------|
| 61 | CH₃O—⟨benzene⟩—NO₂, CH₃ | 515 (CH₃CN) | Bluish-tinged red |
| 62 | C₂H₅O—⟨benzene⟩—NO₂, CH₃ | 516 (CH₃CN) | Bluish-tinged red |
| 63 | ⟨benzene⟩—Cl | 485 (CH₃CN) | Orange |
| 64 | ⟨benzene⟩—CO₂CH₃ | 483 (CH₃CN) | Orange |
| 65 | O₂N—⟨benzene⟩—OCH₃ | 512 (CH₃CN) | Red |

Example 66

Preparation of the coupler component of the formula

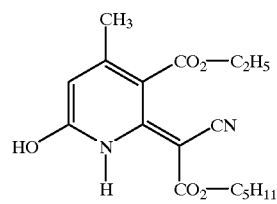

1-Amyl-5-ethyl 3-amino-2-cyano-pentenedioate

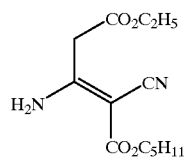

was prepared analougously to Ivanov J. C. et al., Liebigs Ann. Chem. 1983, 753–60 and Mittelbach M. und Juneck H. Liebigs Ann. Chem. 1986, 533–544, by reaction of ethyl 3-amino-ethoxy-2-propenoate hydrochloride with amylcyanoacetate in chloroform in the presence of triethylamine. Further reaction with ethyl acetoacetate analogously to Example 33 gave the coupler component of the above formula.

Example 67

Preparation of the dyestuff of the formula

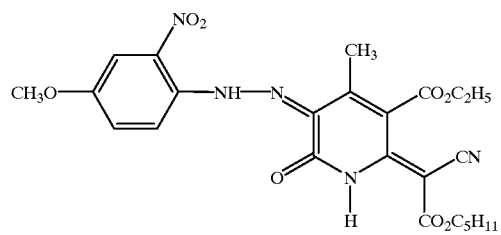

The dyestuff of the above formula was obtained by diazotization of 2-nitro-4-methoxyaniline in hydrochloric acid with 30% strength nitrite solution at 0° C. and subsequent coupling with the coupling component according to Example 66. It dyed polyester in a brilliant red with good fastness properties.

MS, m/z (%): 514 (28), [M$^{+\cdot}$+H], 513 (100) [M$^{+\cdot}$] 399 (12), 370 (26), 168 (29), 43 (36)

$\lambda_{max}$: 515 nm (CH$_3$CN)

Example 68

Preparation of the mixture of couplers of the formula

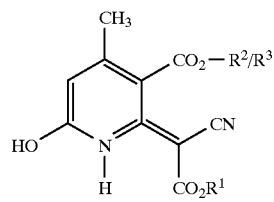

395 g of diamyl 3-amino-2-cyano-pentenedioate (78.7% according to GC) were heated together with 258 ml of ethyl acetoacetate and 154 ml of diazobicycloundecane at 80° C./60 mbar for 8 hours, readily volatile components being destilled off. The excess acetoacetic ester was distilled off under 0.5 mbar/100° C. The brown oil (644 g) which remained was employed directly for the coupling reaction.

MS, m/z (%): 376 (14), [M$^{+\cdot}$], 334 (5) [M$^{+\cdot}$], 307 (5), 262 (12), 219 (23), 218 (22), 193 (15), 192 (67), 151 (48), 137 (20), 126 (27), 123 (27), 98 (19), 96 (17), 71 (20), 55 (33), 43 (100)

The dyestuff of the formula

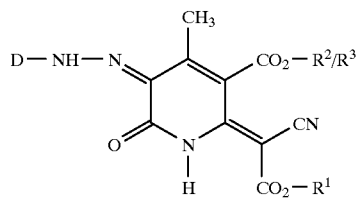

listed on the following Table 5 were obtained by coupling analogously to Example 32 with coupling components which are accessible analogously to the Examples 33, 60, and 68.

TABLE 5

| Ex. No. | D | R¹ | R² | R³ | $\lambda_{max}$ (nm) | Shade on polyester |
|---|---|---|---|---|---|---|
| 69 | CH₃O—[benzene ring with NO₂ and CH₃]— | C₅H₁₁ | C₅H₁₁ 80 | CH₃ 20 | 515 (CH₃CN) | Bluish-tinged red |
| 70 | CH₃O—[benzene ring with NO₂ and CH₃]— | C₅H₁₁ | C₅H₁₁ 85 | C₂H₅ 15 | 515 (CH₃CN) | Bluish-tinged red |
| 71 | C₂H₅O—[benzene ring with NO₂ and CH₃]— | C₅H₁₁ | C₅H₁₁ 85 | C₂H₅ 15 | 516 (CH₃CN) | Bluish-tinged red |
| 72 | CH₃O—[benzene ring with NO₂ and CH₃]— | C₄H₉ | C₄H₉ 80 | CH₃ 20 | 515 (CH₃CN) | Bluish-tinged red |
| 73 | C₂H₅O—[benzene ring with NO₂ and CH₃]— | C₄H₉ | C₄H₉ 80 | CH₃ 20 | 516 (CH₃CN) | Bluish-tinged red |
| 74 | CH₃O—[benzene ring with NO₂ and CH₃]— | C₄H₉ | C₄H₉ 80 | C₂H₅ 20 | 515 (CH₃CN) | Bluish-tinged red |
| 75 | C₂H₅O—[benzene ring with NO₂ and CH₃]— | C₄H₉ | C₄H₉ 80 | C₂H₅ 20 | 516 (CH₃CN) | Bluish-tinged red |
| 76 | O₂N—[benzene ring with CH₃ and OCH₃]— | C₄H₉ | C₄H₉ 80 | C₂H₅ 20 | | Rot |
| 77 | [benzene ring with H₃C, O₂N, OCH₃ and CH₃]— | C₄H₉ | C₄H₉ 80 | C₂H₅ 20 | | Red |

TABLE 5-continued

| Ex. No. | D | R¹ | R² | R³ | λ_max (nm) | Shade on polyester |
|---|---|---|---|---|---|---|
| 78 | 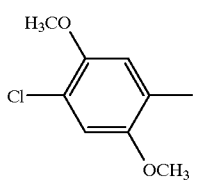 | C₄H₉ | C₄H₉ 80 | C₂H₅ 20 | | Red |
| 79 | 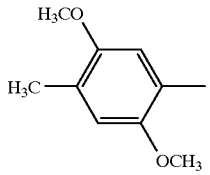 | C₄H₉ | C₄H₉ 80 | C₂H₅ 20 | | Ruby |
| 80 | 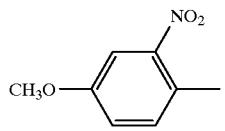 | C₃H₇ | C₃H₂ 80 | C₂H₅ 20 | 515 (CH₃CN) | Bluish-tinged red |
| 81 | 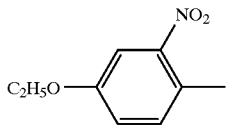 | C₂H₅ | C₄H₉ 80 | C₄H₉ 20 | 516 (CH₃CN) | Bluish-tinged red |
| 82 | 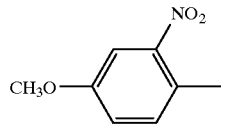 | CH₃ | C₄H₉ 80 | C₄H₉ 20 | 515 (CH₃CN) | Bluish-tinged red |
| 83 | 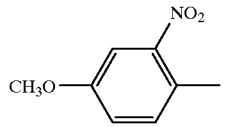 | C₆H₁₃ | C₆H₁₃ 80 | C₂H₅ 20 | 515 (CH₃CN) | Bluish-tinged red |
| 84 | 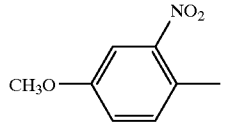 | C₈H₁₇ | C₈H₁₇ 85 | C₂H₅ 20 | 515 (CH₃CN) | Bluish-tinged red |
| 85 | 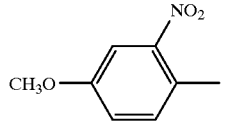 | C₂H₄OCH₃ | C₂H₄OCH₃ 90 | CH₃ 10 | 515 (CH₃CN) | Bluish-tinged red |
| 86 | 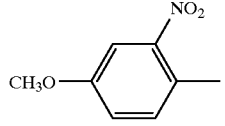 | C₂H₄OC₂H₅ | C₂H₄OC₂H₅ 90 | C₂H₅ 10 | 515 (CH₃CN) | Bluish-tinged red |

Example 87

Preparation of the dyestuffs of the formula

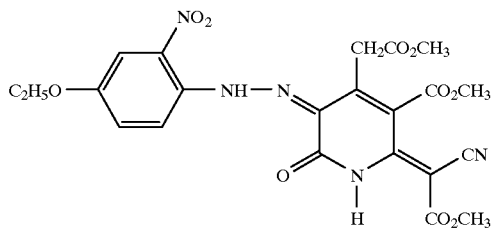

The coupling component was prepared by reaction of dimethylacetonedicarboxylate with dimethyl 3-amino-2-cyano-pentenedioate in the presence of DBU at 100° C. analogously to Example 68. Coupling with diazotized 2-nitro4-ethoxy-aniline gave the dyestuff of the above formula.

MS, m/z (%): 515 (100) [M$^+$], 516 (27), 457 (20), 456 (19), 425 (8), 424 (36), 153 (12)

The dyestuff dyed polyester in a bluish-tinged red with good fastness properties.

Example 88

Preparation of the dyestuff of the formula

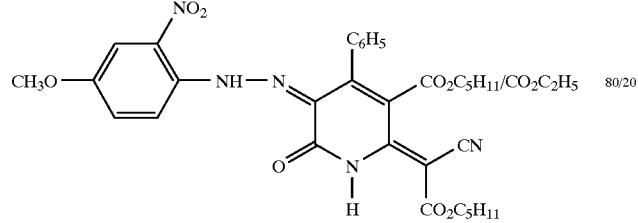

The coupling component was prepared analogously to Example 68 by reaction of ethyl benzoylacetate with diamyl 3-amino-2-cyano-pentenedioate. Subsequent coupling with diazotized 2-nitro-4-methoxyaniline in methanol gave the dyestuff of the above formula in crystalline form.

The dyestuff dyed polyester in a bluish-tinged red with good fastness properties.

MS, m/z (%): 514 (28) [M$^{+\cdot}$+H], 513 (100) [M$^{+\cdot}$], 471 (6), 443 (6), 399 (12), 370 (26), 168 (29), 43 (36)

$\lambda_{max}$ : 497 nm (CH$_3$CN)

The following dyestuffs of the formula

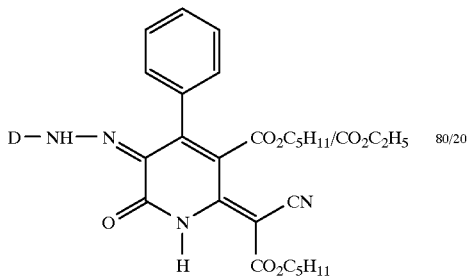

were obtained analogously to Example 88.

TABLE 6

| Ex. No. | D | λ_max nm | Shade on polyester |
|---|---|---|---|
| 89 | 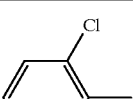 | 470 (CH₃CN) | Scarlet |
| 90 |  | 493 (CH₃CN) | Red |
| 91 | 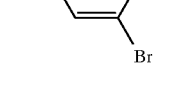 |  | Bluish-tinged red |

Example 92

Preparation of the coupler of the formula

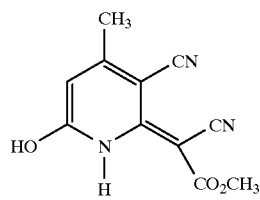

49.5 g of 3-amino-2-methoxycarbonyl-2-pentenedinitrile (H. Junek et al., Synthesis 1977, 560) were heated at the boiling point under reflux with 47 g of ethyl acetoacetate and 30.6 g of piperidine in 300 ml of ethanol for 13 hours. After cooling, the mixture was diluted to a volume of 1.8 l with ice-water and brought to pH=2 with concentrated hydrochloric acid, and the product was filtered off with suction and washed with water. Yield 59 g.

MS, m/z (%): 232 (5), 231 (24) [M⁺·], 187 (42), 172 (36), 160 (14), 144 (21), 132 (13), 92 (26), 91 (29), 84 (23), 59 (100)

¹H-NMR (d₆-DMSO, 300 MHz, ppm): δ=2.15 (s, 3H, CH₃), 3.60 (s, 3H, OCH₃), 5.70 (s, 1H, 5-H), 8.25 (s, (br), 1H, N-H), 12.65 (s, 1H, O-H)

The following dyestuffs of the formula

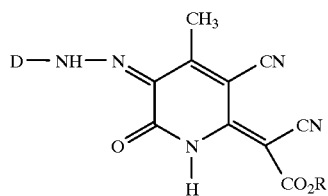

were prepared analogously to Example 32 using coupling components of Example 92 or homologous coupling components.

TABLE 7

| Ex. No. | D | R | λ_max | Shade on polyester |
|---|---|---|---|---|
| 93 | 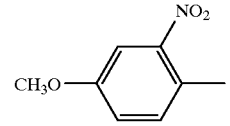 | CH₃ | 520 (CH₃CN) | Bluish-tinged red |
| 94 | 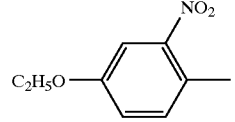 | CH₃ |  | Ruby |
| 95 | 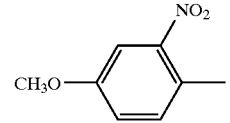 | C₄H₉ |  | Bluish-tinged red |
| 96 | 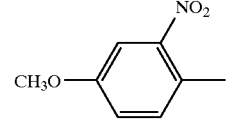 | C₅H₁₁ |  | Bluish-tinged red |
| 97 | 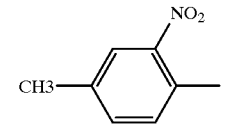 | CH₃ |  | Orange |
| 98 | 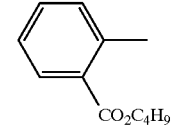 | CH₃ | 443 (NMP) | Scarlet |

TABLE 7-continued

| Ex. No. | D | R | $\lambda_{max}$ | Shade on polyester |
|---|---|---|---|---|
| 99 | 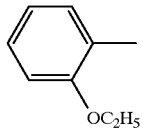 | $CH_3$ | | Ruby |

TABLE 8

Dyestuffs of the formula

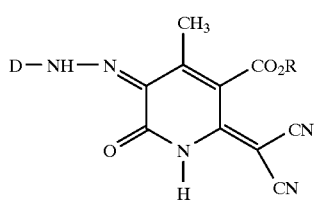

| Ex. No. | D | R | $\lambda_{max}$ | Shade on polyester |
|---|---|---|---|---|
| 100 | 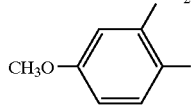 | $C_2H_5$ | | Bluish-tinged red |
| 101 | 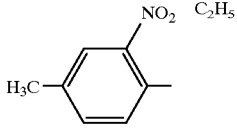 | $C_2H_5$ | 522 (NMP) | Red |
| 102 | 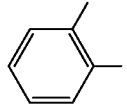 | $C_2H_5$ | | Bluish-tinged red |
| 103 | 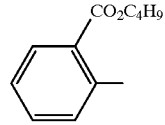 | $C_2H_5$ | | Reddish-tinged orange |
| 104 | 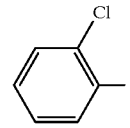 | $C_2H_5$ | 487 ($CH_3CN$) | Reddish tinged orange |
| 105 | 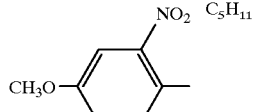 | $C_5H_{11}$ | | Bluish-tinged red |

TABLE 8-continued

Dyestuffs of the formula

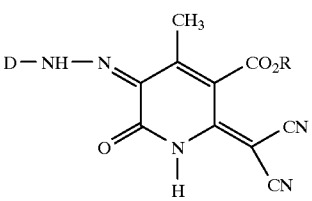

| Ex. No. | D | R | $\lambda_{max}$ | Shade on polyester |
|---|---|---|---|---|
| 106 | 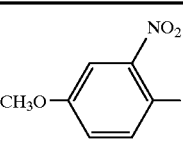 | $C_6H_{13}$ | | Bluish-tinged red |

Example 107

Preparation of the coupler of the formula

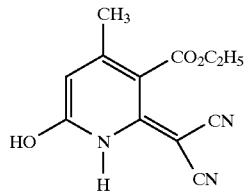

The preparation proceeded analogously to Example 66 by reaction of ethyl 3-amino-4,4-dicyano-3-butenoate (Mittelbach M. and Junek H., Liebigs Ann. Chem. 1986, 533–544) with ethyl acetoacetate.

Example 108

Preparation of the mixture of the couplers of the formula

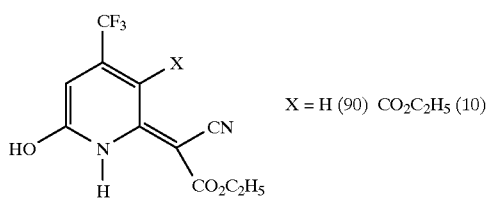

X = H (90)  $CO_2C_2H_5$ (10)

0.25 mol of diethyl 3-amino-2-cyano-pentenediaote ("dimeric ethyl cyanoacetate"), 0.35 mol of methyl trifluoroacetoacetate and 0.25 mol of diazabicycloundecene were heated at 120° C. in 250 ml of dimethylformamide for 12 hours. The solution was topped up to 400 ml with dimethylformamide and employed directly for the coupling reaction. A concentrated sample gave the following mass spectrum.

MS, m/z (%): 346 (1) [$M^{+\cdot}$ X=$CO_2C_2H_5$], 301 (2), 275 (3), 274 (9), [$M^{+\cdot}$ X=H], 255 (7), 246 (5), 203 (11), 202 (89), 184 (14), 173 (20), 152 (44), 123 (27), 96 (27), 29 (100)

TABLE 9

![Structure: D—NH—N= on pyridone ring with CF3, X, and =C(CN)(CO2R) substituents]

| Ex. No. | D | X | R | λmax (nm) | Shade on polyester |
|---------|---|---|---|-----------|-------------------|
| 108 | 2-methyl-5-methoxy-6-nitrophenyl (CH3O-, NO2, CH3-) | H (90) CO2C2H5 (10) | C2H5 | 511 | Bluish-tinged red |
| 109 | 2-methyl-5-ethoxy-6-nitrophenyl (C2H5O-, NO2, CH3-) | H (90) CO2C2H5 (10) | C2H5 | 512 | Bluish-tinged red |
| 110 | 2-methyl-5-methyl-6-nitrophenyl (CH3-, NO2, CH3-) | H (95) CO2CH3 (5) | CH3 | 486 | Orange |
| 111 | 2-methyl-6-(methoxycarbonyl)phenyl (CO2CH3, CH3-) | H (95) CO2CH3 (5) | CH3 | 474 | Orange |
| 112 | 2-methyl-6-ethoxyphenyl (OC2H5, CH3-) | H (100) | CH3 | | Bluish-tinged red |

MS, m/z (%): 409 (24), 408 (100) [M⁺], 275 (6), 135 (12), 120 (19), 108 (27), 93 (17), 65 (11), 58 (17)

$^1$H-NMR (d$_6$-DMF, 300 MHz, ppm): δ = 1.5(t, 3H, OCH$_2$—CH$_3$), 3.94(s, 3H, —OCH$_3$), 4.3(q, 2H, OCH$_2$—CH$_3$), 7.04(s, 1H, hetaromatic H), 7.18(m, 1H, aromatic H), 7.30(m, 2H, aromatic H), 7.70(d, 1H, aromatic H), 11.95(s/br), 1H, N—H), 14.75(s, 1H, OH or NH).

Example 113

Preparation of the dyestuff of the formula

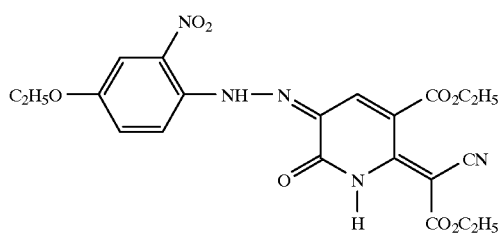

A solution of 18.6 g of ethyl (2'-nitro-4'-ethoxy)-2-phenylazo-formyl acetate, 13.6 g of diethyl 3-amino-2-cyanopentenedioate and 9.1 g of diazabicycloundecene (DBU) in 60 ml of dimethylformamide was heated at 80° C. for 30 minutes. It was diluted with 120 ml of ethanol, 7.3 g of 30% strength hydrochloric acid and 18 ml of water. The precipitate formed was filtered off with suction and washed with ethanol. The dyestuff dyes polyester in a bluish-tinged red with good fastness properties.

UV: 520 nm (CH$_3$CN), 538 nm (DMF)

Example 114

Preparation of the coupler of the formula

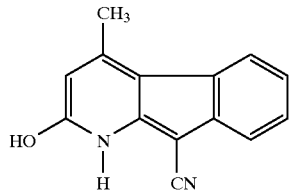

A solution of 7.8 g of 2-amino-3-cyanoindene, 6.8 g of sodium ethylate and 7.8 g of ethyl acetoacetate in 100 ml of ethanol was heated at the boiling point under reflux for 7 hours. The mixture was filtered with suction, the residue was dissolved in water, the solution was brought to pH=1 with hydrochloric acid and the product was filtered off with suction again.

MS, m/z (%): 222 (100) [M$^{+\cdot}$], 221 (5), 194 (6), 193 (10), 179 (7), 166 (7), 140 (4), 139 (4), 84 (8), 67 (5), 38 (5)

TABLE 10

Dyestuffs of the formula

| Ex. No. | D | $\lambda_{max}$ (nm) | Shade on polyester |
|---|---|---|---|
| 115 | ⌬-Cl (2-chlorophenyl) | 469 (CH$_3$CN) | Red-brown |
| 116 | 2,4-dimethylphenyl (H$_3$C-, -CH$_3$) | | Claret |

TABLE 11

Dyestuffs of the formula

| Ex. No. | D | $\lambda_{max}$ (nm) | Colour shade on polyester |
|---|---|---|---|
| 117 | 2-chlorophenyl | | Orange |
| 118 | 2-octyloxyphenyl (OC$_8$H$_{17}$) | | Scarlet |
| 119 | 4-butyl-2-bromophenyl (H$_9$C$_4$-, Br) | | Orange |

TABLE 12

Dyestuffs of the formula

| Ex. No. | D | $\lambda_{max}$ (nm) | Colour shade on polyester |
|---|---|---|---|
| 120 | phenyl | 415 (CH$_3$CN) | Greenish-tinged yellow |
| 121 | 3-bromo-5-nitro-2-nitrophenyl (Br, O$_2$N, NO$_2$) | 562 (DMF) | Claret |

Example 122

Preparation of the coupler of the formula

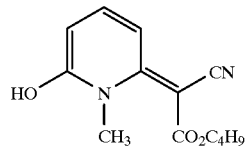

4.3 g of 1-methyl-6-chloro-pyrid-2-one were added to a suspension of 1.8 g of 80% strength sodium hydride in 30 ml of dimethylformamide, and 8.5 g of butyl cyanoacetate were added dropwise in the course of 15 minutes. The temperature rose to 50° C. The mixture was stirred at 50° C. for a further 7 hours, cooled to 20° C. and diluted slowly to a volume of 200 ml with water. The mixture was brought to pH = 7 with hydrochloric acid and extracted with methylene chloride. This extract was discarded. The aqueous phase was brought to pH = 4 and ex- tracted again with methylene chloride. This extract was dried and concentrated. Yield: 2.0 g of oil.

MS, m/z (%): 249 (8), 248 (43) [M⁻], 151 (12), 148 (100), 147 (11), 121 (16), 119 (22), 108 (20), 57 (74), 63 (41)

TABLE 13

Dyestuffs of the formula

D—NH—N, pyridinone-CN/CO₂C₄H₉ structure (CH₃ on N)

| Ex. No. | D | $\lambda_{max}$ (nm) | Colour shade on polyester |
|---|---|---|---|
| 123 | phenyl with NO₂ and CH₃ | | Scarlet |
| 124 | phenyl with NO₂, CH₃O | 515 (CH₃CN) | Bluish-tinged red |
| 125 | phenyl with NO₂ and Cl | | Orange |

Example 126

Preparation of the coupler of the formula

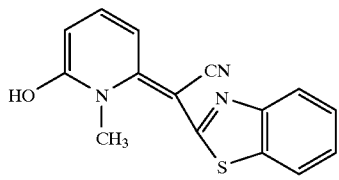

21.8 g of 2-cyanomethyl-benzothiazole and 18 g of 6-chloro-1-methyl-pyrid-2-one were added to a solution of 5 g of sodium hydroxide powder in 125 ml of dimethylformamide and the mixture was stirred at 40° C. for 6 hours. A further 1.8 g of 6-chloro-1-methyl-pyrid-2-one were subsequently added and the mixture was stirred at 40° C. for a further 8 hours. 300 ml of methylene chloride were added and the mixture was discharged onto 400 ml of water. 5.5 g of a crystalline crude product were filtered off with suction, the methylene chloride phase was discarded and the aqueous phase was brought to pH=5, after which a precipitate (B) again precipitated out, this being filtered off with suction and washed with water: 7.8 g yield (B).

MS, m/z (%): 282 (27), 281 (100) [M⁺·], 241 (20), 148 (91), 108 (50), 39 (51)

TABLE 14

Dyestuffs of the formula

D—NH—N, pyridinone-benzothiazole-CN structure (CH₃ on N)

| Ex. No. | D | $\lambda_{max}$ (nm) | Colour shade on polyester |
|---|---|---|---|
| 127 | phenyl with NO₂ and Cl | | Claret |
| 128 | phenyl with NO₂ and CH₃ | | Claret |

Example 129

Preparation of the coupler of the formula

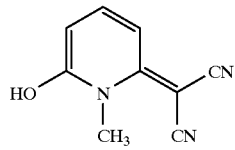

A mixture of 37.4 g of 2,6-dichloropyridine and 47.5 ml of dimethyl sulphate was stirred at 100° C. for 24 hours. After cooling, it was diluted with 75 ml of dimethylformamide, and a solution of 16.5 g of malononitrile in 25 ml of dimethylformamide and then 86.6 ml of triethylamine were added dropwise, while cooling with ice. The mixture was subsequently stirred for 20 hours and 14.7 g of a yellow product of the formula

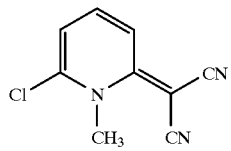

were then filtered off with suction. A further 4 g were to be obtained by dilution of the filtrate with ice-water and acidification to pH=1.

MS (CI), m/z (%): 194 (35), 192 (100) [M$^{+\cdot}$], 158 (32)

76.6 g of [1-methyl-6-chloro-2(1)-pyridinylidene] malononitrile were stirred in 400 ml of water and 400 ml of N-methylpyrrolidone at 80° C. for 10 hours and at 90° C. for 5 hours, pH=10 being maintained by dropwise addition of 30% strength sodium hydroxide solution via a titrator. The mixture was topped up to a volume of 1200 ml with water and brought to pH=1 with concentrated hydrochloric acid, and the product was filtered off with suction and washed with water. Yield: 63.5 g.

MS, m/z (%): 173 (100) [M$^{+\cdot}$], 146 (25), 145 (37), 144 (37), 130 (14), 119 (25), 118 (33), 108 (45), 39 (58).

$^1$H-NMR (d$_6$-DMSO, 300 MHz, ppm): δ=3.73 (s, 3H, N-CH$_3$), 6.15 (d, I=7.5 Hz, 1H, 5-H), 6.53 (d, I=7.5 Hz, 1H, 3-H), 7.48 (dd, I=7.5 Hz, 1H, 4-H), 11.80 (s(br), OH, H$_2$O).

TABLE 15

Dyestuffs of the formula

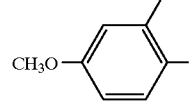

| Ex. No. | D | λ$_{max}$ (nm) | Colour shade on polyester |
|---|---|---|---|
| 130 | 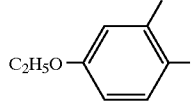 | 516 (CH$_3$CN) | Bluish-tinged red |
| 131 | 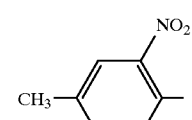 | 517 (CH$_3$CN) | Bluish-tinged red |
| 132 | 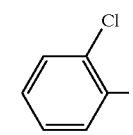 | | Orange |
| 133 | 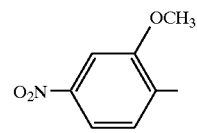 | 490 (CH$_3$CN) | Scarlet |
| 134 | 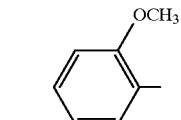 | | Orange |
| 135 | 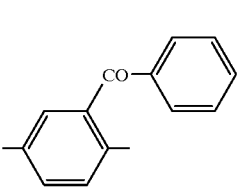 | 498 (CH$_3$CN) | Yellow-tinged red |
| 136 | | 485 (CH$_3$CN) | Orange |
| 137 | | | Orange |

TABLE 15-continued

Dyestuffs of the formula

D—NH—N, 2-oxo-1-methyl-pyridinylidene-malononitrile structure

| Ex. No. | D | λ_max (nm) | Colour shade on polyester |
|---|---|---|---|
| 138 | 2-(CO$_2$C$_2$H$_5$)phenyl | 477 (CH$_3$CN) | Orange |

TABLE 15-continued

Dyestuffs of the formula

D—NH—N, 2-oxo-1-methyl-pyridinylidene-malononitrile structure

| Ex. No. | D | λ_max (nm) | Colour shade on polyester |
|---|---|---|---|
| 139 | 2-Cl-5-NO$_2$-4-OCH$_3$-phenyl | | Scarlet |

TABLE 16

Dyestuffs of the formula

D—NH—N with A$^1$, A$^2$, A$^5$ substituted pyridinylidene malononitrile

| Ex. No. | D | A$^1$ | A$^2$ | A$^5$ | λ_max (nm) | Colour shade on polyester |
|---|---|---|---|---|---|---|
| 140 | 2-NO$_2$-4-OCH$_3$-phenyl | H | H | C$_2$H$_5$ | 516 (CH$_3$CN) | Bluish-tinged red |
| 141 | 2-NO$_2$-4-OC$_2$H$_5$-phenyl | CH$_3$ | H | CH$_3$ | 508 | Yellowish-tinged red |
| 142 | 2-NO$_2$-4-OCH$_3$-phenyl | CH$_3$ | CN | CH$_3$ | | Bluish-tinged red |
| 143 | 2-NO$_2$-4-OCH$_3$-phenyl | H | H | C$_3$H$_7$ | 516 | Bluish-tinged red |

TABLE 16-continued

Dyestuffs of the formula

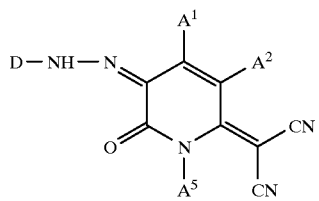

| Ex. No. | D | $A^1$ | $A^2$ | $A^5$ | $\lambda_{max}$ (nm) | Colour shade on polyester |
|---|---|---|---|---|---|---|
| 144 | 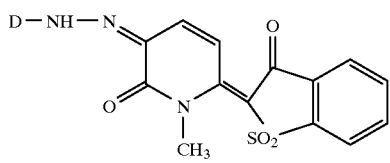 | H | H | $C_4H_9$ | 516 | Bluish-tinged red |

TABLE 17

Dyestuffs of the formula

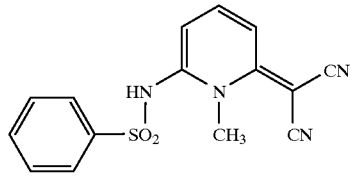

| Ex. No. | D | $\lambda_{max}$ (nm) | Colour shade on polyester |
|---|---|---|---|
| 145 | ![CO2CH3 phenyl] | | Red |
| 146 | ![CN phenyl] | | Red |
| 147 | ![Cl phenyl] | | Red |
| 148 | ![NO2 phenyl] | | Red |

Example 149

Preparation of a coupler 15.7 g of benzenesulphonamide were added to a solution of 5.4 g of sodium methylate in 120 ml of methanol and the mixture was boiled under reflux for 2 hours, the benzenesulphonamide dissolving. The solution was concentrated to dryness, the residue was dissolved in 75 ml of N-methylpyrrolidone and a solution of 19.2 g of [1-methyl-6-chloro-2(1H)-pyridinylidene]malononitrile (see Example 129) in 75 ml of N-methylpyrrolidone was allowed to run in. After 20 hours at room temperature, a further 2.7 g of sodium methylate and 3.9 g of benzenesulphonamide were added and the mixture was heated at 50° C. for 5 hours and stirred at room temperature for 60 hours. It was diluted with 600 ml of ice-water and brought to pH=1 with hydrochloric acid, and the product was filtered with suction and washed with water. Yield 15 g.

$^1$H-NMR ($d_6$-DMSO, 300 MHz, ppm): δ=3.75 (s, 3H, N-CH$_3$), 6.38 (d, I=7.5 Hz, 1H, heterocyclic H), 6.45 (d, I=7.5 Hz, 1H, heterocyclic H), 7.30 (dd, I=7.5 Hz, 1H, heterocyclic H), 7.53 (m, 3H, aromatic H), 7.78 (m, 2H, aromatic H), 9.48 (s(br), 1H, N-H).

TABLE 18

Dyestuffs of the formula

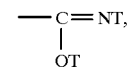

| Ex. No. | D | λ_max (nm) | Colour shade on polyester |
|---|---|---|---|
| 150 | 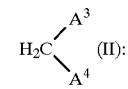 | | Bluish-tinged red |
| 151 | 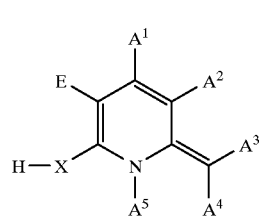 | | Yellowish-tinged red |

Example 152

10 g of polyester fabric are introduced at a temperature of 60° C. into 200 ml of a dye liquor which comprises 0.3% of the finely dispersed dyestuff of Example No. 134, based on the polyester fabric, and in which the pH is adjusted to 4.5 by means of acetic acid. The fabric is treated at 60° C. for 5 minutes, the temperature of the liquor is then increased to 135° C. in the course of 30 minutes and kept at this temperature for 60 minutes, and the liquor is then allowed to cool to 60° C. in the course of 20 minutes.

Thereafter, the dyed polyester fabric is purified reductively by being treated at 65° C. for 15 minutes in 200 ml of a liquor which comprises 5 ml/l of 32% strength by weight sodium hydroxide solution, 3 g/l of sodium dithionite and 1 g/l of an addition product of 48 ml of ethylene oxide on 1 mol of castor oil. Finally, the fabric is rinsed, neutralized with dilute acetic acid, rinsed again and dried. A brilliant orange dyeing with good fastness properties is obtained.

What is claimed is:

1. A compound of the formula (V)

(V)

wherein

E is a substituent which is replaceable by electrophilic substitution

X is O, NH, NT, NCOT, NCO$_2$T or NSO$_2$T, $A^1$ and $A^2$ independently of one another denote H or a radical of the formula T, -COH, -CO-T, -CO$_2$-T, -CN, -CONH$_2$, -CONHT, -CONT$_2$, CF$_3$, -NO$_2$, NO, -SO$_2$T, -OH, -OT, OCOT, -OCO$_2$T, OSO$_2$T, Cl, Br or I, wherein T is T$^1$, T$^2$, T$^3$, T$^4$ or T$^5$, where T$^1$=alkyl, cycloalkyl or aralkyl, T$^2$=alkenyl, T$^3$=alkinyl, T$^4$=aryl, T$^5$=hetaryl, $A^3$ and $A^4$ independently of one another are, -CN, -CO$_2$T, -CONH$_2$, -CONHT, -CONT$_2$, CF$_3$, -CHO, -COT, -SO$_2$T, -SO$_3$T$^4$, -SO$_3$T$^5$, -SO$_2$NH$_2$, SO$_2$NHT, -SO$_2$NT$_2$, -SOT, -CH=NH, -CH=NT, -CT=NH, -CT=NT, $$-\underset{\underset{OT}{|}}{C}=NT,$$

-CO-CO$_2$T, -NO$_2$, -NO, -T$^4$ or T$^5$, wherein $A^3$ and $A^4$ do not simultaneously represent T$^4$ or T$^5$, or T$^4$ and T$^5$, or $A^3$ and $A^4$, together with the C atom to which they are bonded, represent a cyclic methylene-active compound of the formula (IIa) to (IIv), where these radicals are shown in the form of $$H_2C\begin{matrix}A^3\\ \\A^4\end{matrix}\quad (II):$$

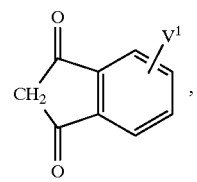 (IIa)

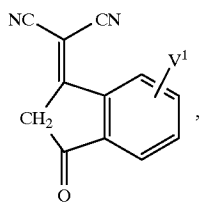 (IIb)

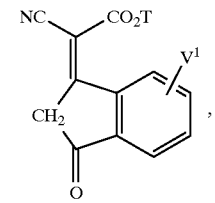 (IIc)

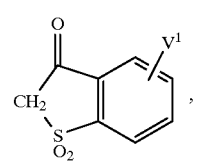 (IId)

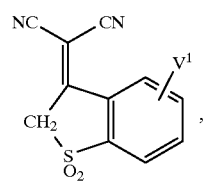 (IIe)
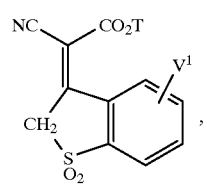 (IIf)
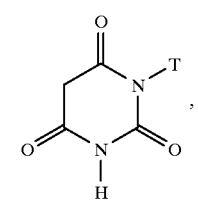 (IIg)
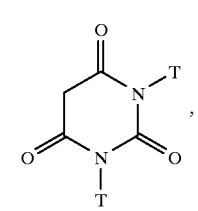 (IIh)
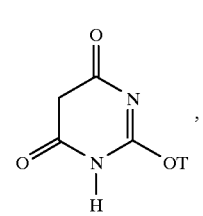 (IIi)
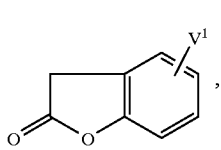 (IIj)
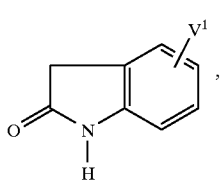 (IIk)
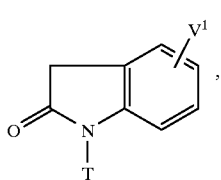 (IIl)
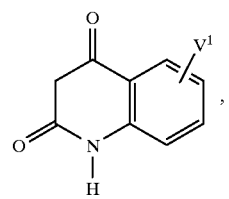 (IIm)
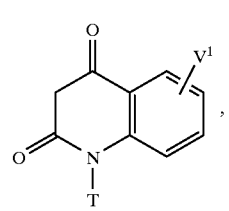 (IIn)
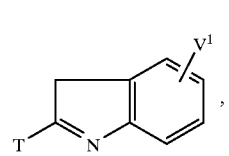 (IIo)
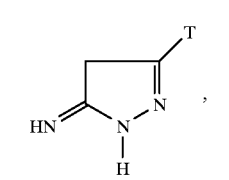 (IIp)
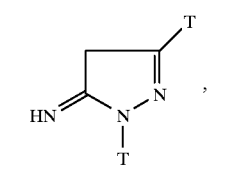 (IIq)
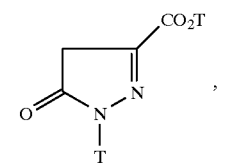 (IIr)
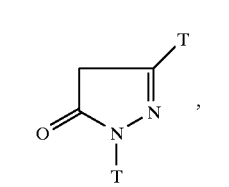 (IIs)
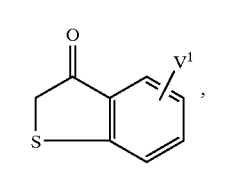 (IIt)

-continued

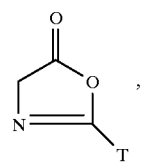
(IIu)

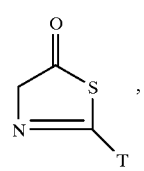
(IIv)

wherein $V^1$ represents H, Cl, Br, $CH_3$, $-CO_2T^1$, -CN, $-NO_2$, $-CF_3$ or $-SO_2T^1$, $A^5$ represents H or a radical of the formula T, $-OT^1$, $-NH_2$, -NHT, $-NT_2$, -NHCOH, -NHCOT, -N=CH-T, $-N=CT_2$ or $NHSO_2T$, or $A^1$ and $A^2$ or $A^2$ and $A^3$, together with the particular atoms in between, form an unsaturated, unsubstituted or substituted 5- or 6-membered carbo- or heterocyclic radical, where, in the case of ring formation with participation of one of the radicals $A^3$ or $A^4$, the other particular radical is defined above, and where the radicals $A^1$ to $A^5$ do or do not contain one or more $SO_3H$, COOH or K and B groups, wherein K and B have the above meanings.

2. A process for the preparation of a compound of the formula (V) of claim 1 in the form of the compound Va or Vb, wherein X represents O or NH, wherein acetic acid derivatives of the formula IXa or IXb are reacted with enamines of the formula (VIII)

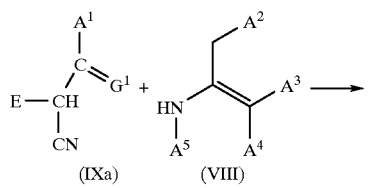
(IXa)   (VIII)

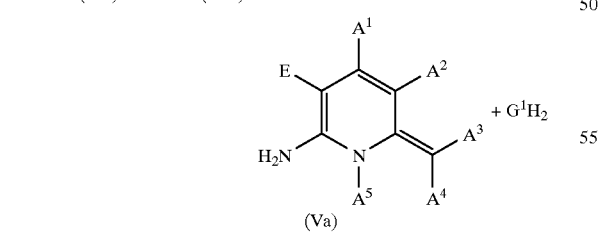
(Va)

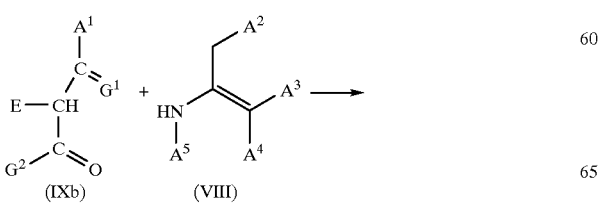
(IXb)   (VIII)

-continued

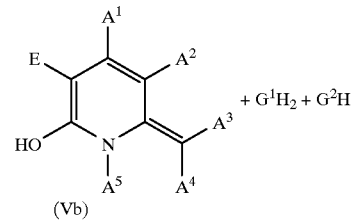
(Vb)

wherein $A^1$ and $A^2$ independently of one another denote H or H or a radical of the formula -T, -COH, -CO-T, $-CO_2$-T, -CN, $CONH_2$, -CONHT, $-CONT_2$, $-CF_3$, $-NO_2$, -NO, $-SO_2T$, -OH, -OT, OCOT, $-OCO_2T$, $OSO_2T$-, Cl, Br or I.

$A^3$ and $A^4$ independently of one another are -CN, $-CO_2T$, $-CONH_2$, -CONHT, $-CONT_2$-, $CF_3$, -CHO, -COT, $-SO_2T$, $-SO_3T^4$, $-SO_3T^5$, $-SO_2NH_2$-, $SO_2NHT$, $-SO_2NT_2$, -SOT, -CH=NH, -CH=NT, -CT=NH, -CT=NT,

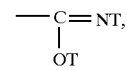

$-CO-CO_2T$, $-NO_2$, -NO, $T^4$ or $T^5$, wherein $A^3$ and $A^4$ do not simultaneously represent $T^4$ or $T^5$ or $T^4$ and $T^5$, or $A^3$ and $A^4$, together with the C atom to which they are bonded, represent a cyclic methylene-active compound of the formula (IIa) to (IIv), where these radicals are shown in the form of

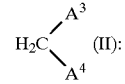
(II):

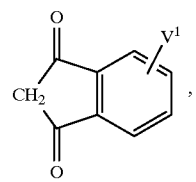
(IIa)

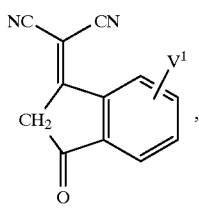
(IIb)

-continued
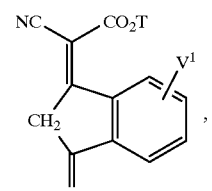 (IIc)
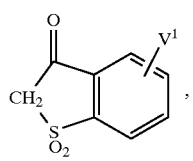 (IId)
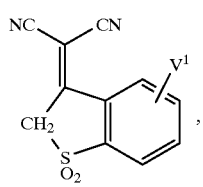 (IIe)
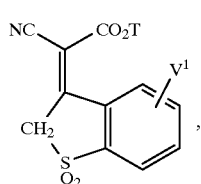 (IIf)
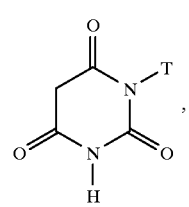 (IIg)
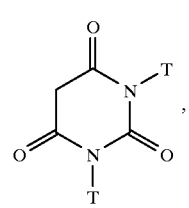 (IIh)
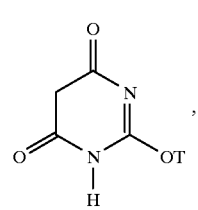 (IIi)
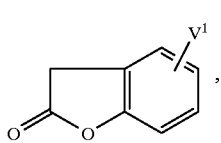 (IIj)
-continued
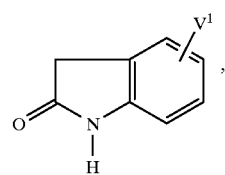 (IIk)
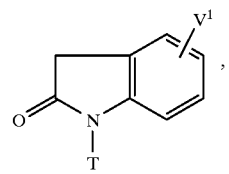 (IIl)
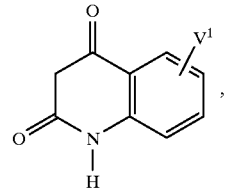 (IIm)
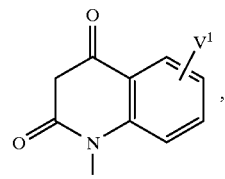 (IIn)
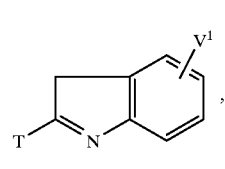 (IIo)
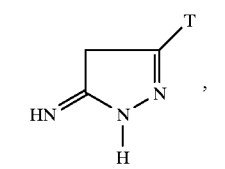 (IIp)
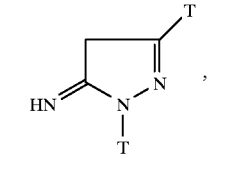 (IIq)
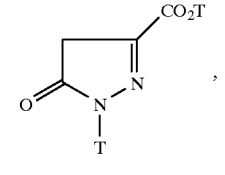 (IIr)

-continued (IIs)

[structure: pyrazolone with T at position 3, T on N1, =O at 5]

(IIt)

[structure: benzothiophenone with V¹ substituent]

(IIu)

[structure: oxazolinone with T substituent]

(IIv)

[structure: thiazolinone with T substituent]

wherein
  $V^1$ represents H, Cl, Br, $CH_3$, $-CO_2T^1$, -CN, $-NO_2$, $-CF_3$ or $-SO_2T^1$,
  $A^5$ represents H or a radical of the formula T, $-OT^1$, $-NH_2$, -NHT, $-NT_2$, -NHCOH, -NHCOT, -N=CH-T, $-N=CT_2$ or $NHSO_2T$,
wherein
  T represents $T^1$ to $T^5$,
  $T^1$=alkyl, cycloalkyl or aralkyl,
  $T^2$=alkenyl,
  $T^3$=alkinyl,
  $T^4$=aryl,
  $T^5$=hetaryl
or at least one pair of
  $A^1$ and $A^2$,
  $A^2$ and $A^3$ and
  $A^4$ and $A^5$,
together with the particular atoms in between, form an unsaturated, unsubstituted or substituted 5- or 6-membered carbo- or heterocyclic radical, with the proviso that if a ring is formed with participation of one of the two radicals $A^3$ and $A^4$, the radical which does not participate is defined above,
  X represents O, NH, NT, NCOT, $NCO_2T$ or $NSO_2T$,
  E represents a substituent which is replaceable by electrophilic substitution,
  $G^1$ denotes O, NH or NT and
  $G^2$ represents OT, $NH_2$ or NHT, wherein T has the above meaning.

3. Process for the preparation of compounds of the formula V which correspond to the formula X, wherein trifluoroacetic esters of the formula (XI) are subjected to a condensation reaction with dimeric cyanoacetic acid esters of the formula (XII)

[reaction scheme: (XI) $CF_3$-CO-$CH_2$-CO-$OT^1$ + (XII) dimeric cyanoacetic ester with $H_2N$, CN, $CO_2T^1$ groups → (X) 4-$CF_3$-6-hydroxy pyridinone with =C(CN)($CO_2T^1$) substituent + $H_2O$ + 2$HOT^1$ + $CO_2$]

wherein $T^1$ is alkyl, cycloalky or aralkyl.

4. A process for the preparation of a compound of the formula (V)

(V)

[structure: pyridine ring with $A^1$, $A^2$, $A^3$, $A^4$, $A^5$, E, H-X substituents]

wherein
  $A^5$ represents $T^1$, $T^2$ or $T^3$, wherein a pyridium salt of the formula (XIII)

(XIII)

[structure: pyridinium cation with $A^1$, $A^2$, E, $Y^1$, $Y^2$, $A^5$ substituents and $An^\ominus$ anion]

wherein
  $A^1$ and $A^2$ independently of one another denote H or a radical of the formula T, -COH, -CO-T, $-CO_2$-T, -CN, $-CONH_2$, -CONHT, $-CONT_2$, $-CF_3$, $-NO_2$, NO, $-SO_2T$, -OH, -OT, OCOT, $-OCO_2T$, $OSO_2T$, Cl, Br or I,
  $A^3$ and $A^4$ independently of one another denote an electron-withdrawing radical, or, together with the common C atom, form a cyclic methylene-active compound, -CN, $-CO_2T$, $-CONH_2$, -CONHT, $-CONT_2$, $-CF_3$, -CHO, -COT, $-SO_2T$, $SO_3T^4$, $-SO_3T^5$, $-SO_2NH_2$, $-SO_2NHT$, $-SO_2NT_2$, -SOT, -CH=NH, -CH=NT, -CT=NH, -CT=NT, $$-\underset{OT}{\overset{|}{C}}=NT,$$

$-CO-CO_2T$, $-NO_2$, -NO, $T^4$ or $T^5$,
wherein $A^3$ and $A^4$ do not simultaneously represent $T^4$ or $T^5$ or $T^4$ and $T^5$, or
$A^3$ and $A^4$, together with the C atom to which they are bonded, represent a cyclic methylene-active compound of the formula (IIa) to (IIv).
where these radicals are shown in the form of
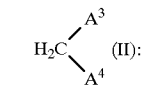
(II):
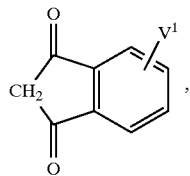
(IIa)
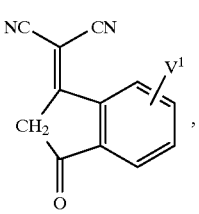
(IIb)
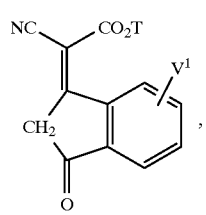
(IIc)
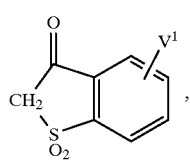
(IId)
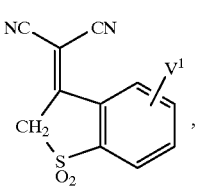
(IIe)
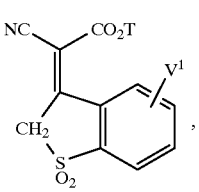
(IIf)
-continued
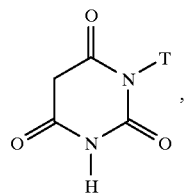
(IIg)
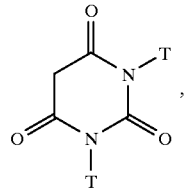
(IIh)
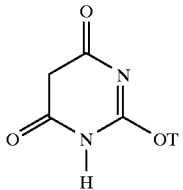
(IIi)
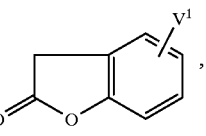
(IIj)
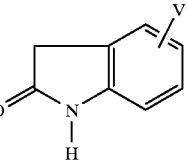
(IIk)
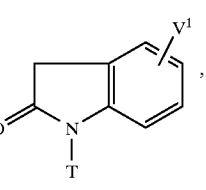
(IIl)
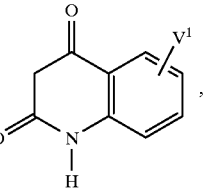
(IIm)
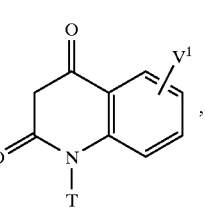
(IIn)

-continued

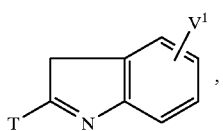 (IIo)

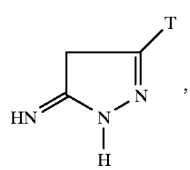 (IIp)

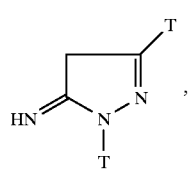 (IIq)

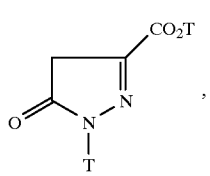 (IIr)

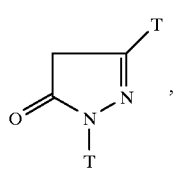 (IIs)

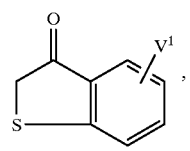 (IIt)

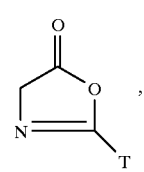 (IIu)

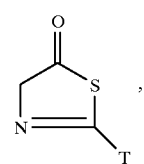 (IIv)

wherein
$V^1$ represents H, Cl, Br, $CH_3$, $-CO_2T^1$, -CN, $-NO_2$, $-CF_3$ or $SO_2T^1$,
or at least one pair of
$A^1$ and $A^2$,
$A^2$ and $A^3$ and
$A^4$ and $A^5$,
together with the particular atoms in between, form an unsaturated, unsubstituted or substituted 5- or 6-membered carbo- or heterocyclic radical, with the proviso that if a ring is formed with participation of one of the two radicals $A^3$ and $A^4$, the radical which does not participate is defined above, E represents a substituent is be replaceable by electrophilic substitution,
$An^\ominus$ is an anion,
T represents $T^1$ to $T^5$,
$T^1$=alkyl, cycloalkyl or aralkyl, and, where
$T^2$=alkenyl,
$T^3$=alkinyl,
$T^4$=aryl,
$T^5$=hetaryl
$Y^1$ and $Y^2$ independently of one another represent, F, Cl, Br, I, $-OSO_2T$, -OT, -ST or $-SO_2T$
is reacted with a compound of the formula (II)

 (II)

wherein
$A^3$ and $A^4$ are defined above [independently of one another are denote an electron-withdrawing radical, or, together with the common C atom, form a cyclic methylene-active compound,
$A^5$ represents H or a radical of the formula T, $-OT^1$, $-NH_2$, -NHT, $-NT_2$, -NHCOH, -NHCOT, -N=CH-T, $-N=CT_2$ or $NHSO_2T$,
wherein
$T^1$=alkyl, cycloalkyl or aralkyl, and T represents $T^1$ or can assume the meaning of $T^2$ to $T^5$, where
$T^2$=alkenyl,
$T^3$=alkinyl,
$T^4$=aryl,
$T^5$=hetaryl
or at least one pair of
$A^1$ and $A^2$
$A^2$ and $A^3$ and
$A^4$ and $A^5$, together with the particular atoms in between, form an unsaturated, unsubstituted or substituted 5- or 6-membered carbo- or heterocyclic radical, with the proviso that if a ring is formed with participation of one of the two radicals $A^3$ and $A^4$, the radical which does not participate is defined above,
X represents O, NH, NT, NCOT, $NCO_2T$ or $NSO_2T$,
to give a compound of the formula (XIV)

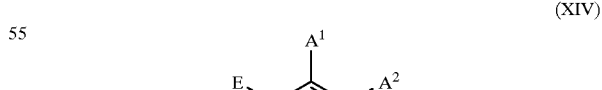 (XIV)

and this is reacted with compounds of the formula (XV)

$XH_2$ (XV)

wherein

X represents O, NH, $NT^1$, $NCO_2T$ or $NSO_2T$,
to give a compound of the formula (V).

5. The process according to claim 4, wherein $Y^1$ and $Y^2$ independently from another represent F, Cl, I, $-OSO_2T$, -OT, -ST or $-SO_2T$.

6. The process according to claim 4, wherein
$An^\ominus$ represents $Cl^\ominus$, $Br^\ominus$, $I^\ominus$, $T^1OSO_3^\ominus$ or $TSO_3^\ominus$.

7. A process for the preparation of the coupling components of the formula (V), wherein $A^5$ represents T, wherein a pyridine derivative of the formula (XVII) is reacted with a compound of the formula (II):

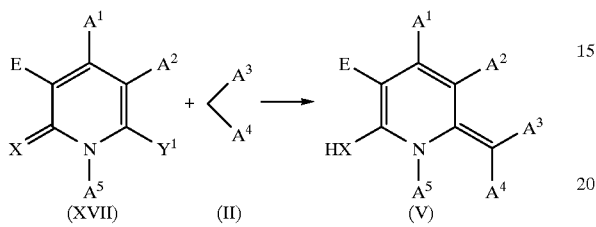

wherein

X=O, $A^1$ and $A^2$ independently of one another denote H or a radical of the formula -T, -COH, -CO-T, $-CO_2$-T, -CN, $-CONH_2$, -CONHT, $-CONT_2$, $-CF_3$, $-NO_2$, -NO, $-SO_2T$, -OH, -OT, -OCOT, $-OCO_2T$, $-OSO_2T$, Cl, Br or I, $A^3$ and $A^4$ independently of one another are -CN, $-CO_2T$, $-CONH_2$, -CONHT, $-CONT_2$, $-CF_3$, -CHO, -COT, $-SO_2T$, $-SO_3T^4$, $-SO_3T^5$, $-SO_2NH_2$, $-SO_2NHT$, $-SO_2NT_2$, SOT, $-CH=NH$, $-CH=NT$, $-CT=NH$, $-CT=NT$,

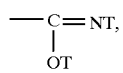

$-CO-CO_2T$, $-NO_2$, -NO, $T^4$ or $T^5$,
wherein $A^3$ and $A^4$ do not simultaneously represent $T^4$ or $T^5$ or $T^4$ and $T^5$, or $A^3$ and $A^4$, together with the C atom to which they are bonded, represent a cyclic methylene-active compound of the formula (IIa) to (IIv), where these radicals are shown in the form of

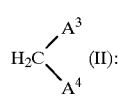

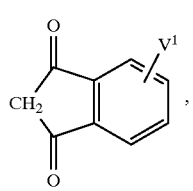

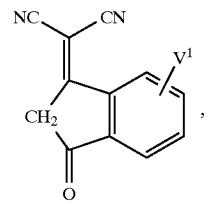

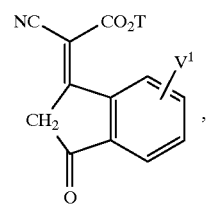

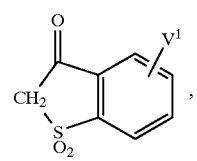

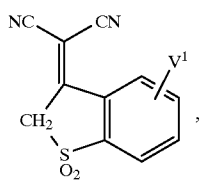

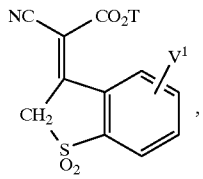

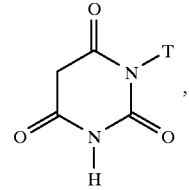

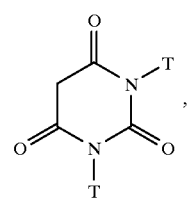

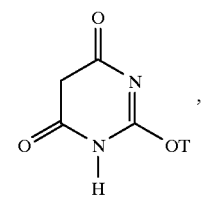 (IIi)

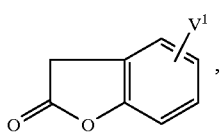 (IIj)

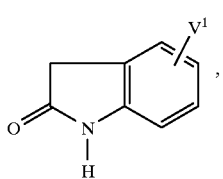 (IIk)

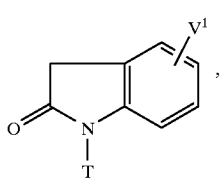 (IIl)

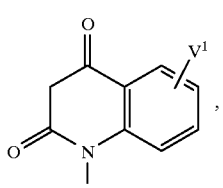 (IIm)

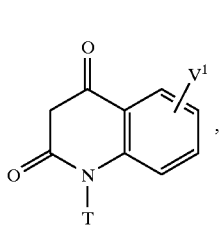 (IIn)

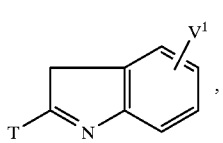 (IIo)

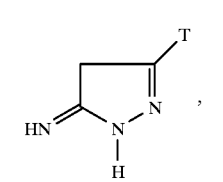 (IIp)

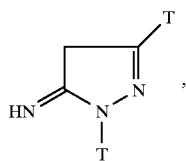 (IIq)

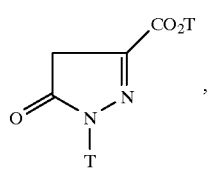 (IIr)

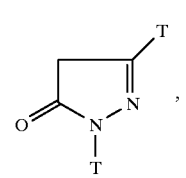 (IIs)

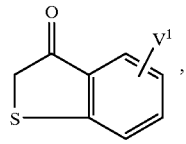 (IIt)

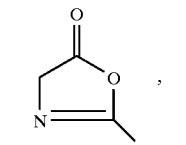 (IIu)

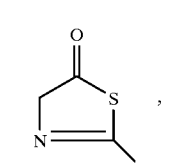 (IIv)

wherein $V^1$ represents H, Cl, Br, CH$_3$, -CO$_2$T$^1$, -CN, -NO$_2$, -CF$_3$ or -SO$_2$T$^1$, and A$^5$ represents T and T represents T$^1$ to T$^5$, where T$^1$=alkyl, cycloalkyl or aralkyl, T$^2$=alkenyl, T$^3$=alkinyl, T$^4$=aryl, T$^5$=hetaryl or at least one pair of A$^1$ and A$^2$, A$^2$ and A$^3$ and A$^4$ and A$^5$, together with the particular atoms in between, form an unsaturated, unsubstituted or substituted 5- or 6-membered carbo- or heterocyclic radical, with the proviso that if a ring is formed with participation of one of the two radicals A$^3$ and A$^4$, the radical which does not participate is defined above E represents a substituent which is replaceable by electrophilic substitution.

8. A process for the preparation of a compound of the formula (V) which corresponds to the formula (XX), wherein $A^5$ represents $T^1$, $T^2$ or $T^3$, wherein 2-methylpyridone of the formula (XVIII) is reacted with phthalic acid esters of the formula (XIX) in the presence of a base

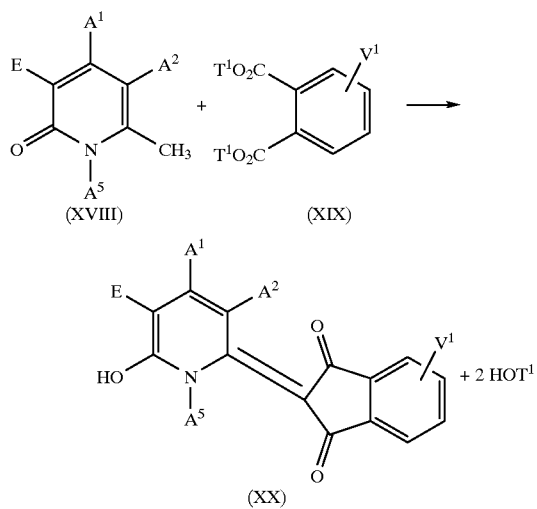

wherein $A^1$ represents H, T, -COH, -COT, -$CO_2$T, -CN, -$CONH_2$, -CONHT, -$CONT_2$, $CF_3$, OH or halogen, $A^2$ represents H, T, -COH, -COT, -CN, -$CO_2$T, -$CONH_2$, -CONHT, -$CONT_2$, -$CF_3$, -$NO_2$, -NO, Cl, Br or I, $A^5$ represents H or a radical of the formula T, -$OT^1$, -$NH_2$, -NHT, -$NT_2$, -NHCOH, -NHCOT, -N=CH-T, -N=$CT_2$ or $NHSO_2$T, $T^1$ denotes $C_1$-$C_{10}$-alkyl, $C_5$-$C_7$-cycloalkyl or $C_6$-$C_{10}$-aryl-$C_1$-$C_6$-alkyl, which are unsubstituted or substituted by one or more substituents from the group consisting of -OH, -$C_1$-$C_{10}$-alkoxy, -O{$(CH_2)_{2-10}$-O}$_{1-6}$-alkyl, -OCOT, -$OSO_2$T, -O-($CH_2$ $CH_2$O)$_{1-6}$ COT, -COT, -$SO_2$T, -$CO_2$T, -CN, -$CO_2$H, -$CONT_2$, -$CF_3$, Cl, Br and I, T represents $T^{1'}$, $T^2$, $T^3$, $T^4$ or $T^5$, $T^{1'}$=alkyl, cycloalkyl or aralkyl, $T^2$=alkenyl, $T^3$=alkinyl, $T^4$=aryl, $T^5$=hetaryl E represents a substituent which is replaceable by electrophilic substitution and $V^1$ represents H or a substituent.

9. The process as claimed in claim 8, wherein is $T^1$ is -$C_1$-$C_{10}$-alkoxy-$C_2$-$C_5$-alkoxy, -$C_1$-$C_5$-alkoxy-$C_2$-$C_5$-alkoxy-$C_2$-$C_5$-alkoxy or -O-($CH_2$-$CH_2$O)$_{1-6}$-alkyl.

* * * * *

UNITED STATES PATENT AND TRADEMARK OFFICE
CERTIFICATE OF CORRECTION

PATENT NO.  : 5,955,615
DATED       : September 21, 1999
INVENTOR(S) : Hamprecht It is certified that error appears in the above-identified patent and that said Letters Patent is hereby corrected as shown below:

In column 77, line 36, please delete "K and B have the above meanings" and replace with - -$K^+$ is -$NH_3^+$, -$NHT_2^+$, -$NH_2T^+$, $NT_3^+$ or a cycloimmonium ion and $B^-$ is an anion- - .

Signed and Sealed this

Seventh Day of November, 2000

*Attest:*

Q. TODD DICKINSON

*Attesting Officer*     *Director of Patents and Trademarks*